United States Patent
Matsuura et al.

(10) Patent No.: US 10,243,145 B2
(45) Date of Patent: *Mar. 26, 2019

(54) ORGANIC ELECTROLUMINESCENCE DEVICE AND ORGANIC LIGHT EMITTING MEDIUM

(71) Applicant: IDEMITSU KOSAN CO., LTD., Chiyoda-ku (JP)

(72) Inventors: Masahide Matsuura, Chiba (JP); Masakazu Funahashi, Chiba (JP); Kenichi Fukuoka, Chiba (JP); Chishio Hosokawa, Chiba (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/925,968

(22) Filed: Mar. 20, 2018

(65) Prior Publication Data
US 2018/0212152 A1 Jul. 26, 2018

Related U.S. Application Data

(60) Continuation of application No. 15/638,805, filed on Jun. 30, 2017, now Pat. No. 9,960,358, which is a
(Continued)

(30) Foreign Application Priority Data

Jul. 19, 2002 (JP) .................. 2002-211308

(51) Int. Cl.
H01L 51/54 (2006.01)
C09K 11/06 (2006.01)
(Continued)

(52) U.S. Cl.
CPC ........ H01L 51/0058 (2013.01); C07C 13/567 (2013.01); C07C 13/72 (2013.01); C07C 15/28 (2013.01); C07C 15/30 (2013.01); C07C 15/38 (2013.01); C07C 15/52 (2013.01); C09K 11/06 (2013.01); H01L 51/006 (2013.01); H01L 51/0052 (2013.01); H01L 51/0054 (2013.01); H01L 51/0056 (2013.01); H01L 51/0072 (2013.01); H05B 33/14 (2013.01); B82Y 30/00 (2013.01); C07C 2603/46 (2017.05); C07C 2603/50 (2017.05); C09K 2211/1007 (2013.01); C09K 2211/1011 (2013.01); C09K 2211/1014 (2013.01); C09K 2211/1018 (2013.01); H01L 51/0055 (2013.01); H01L 51/0059 (2013.01); H01L 51/0062 (2013.01);
(Continued)

(58) Field of Classification Search
CPC ....... C07C 13/00; C07C 13/32; C07C 13/567; C07C 13/62; C07C 13/72; C07C 15/20; C07C 15/27; C07C 15/28; C07C 15/30; C07C 15/38; C07C 2103/00; C07C 2103/42; C07C 2103/44; C07C 2103/48; C07C 2103/50; C07C 2103/52; C07C 2103/54; H05B 33/14; Y10S 428/917; Y10S 977/755; B82Y 30/00; C09K 11/06; C09K 2211/00; C09K 2211/10; C09K 2211/1003; C09K 2211/1007; C09K 2211/1011; C09K 2211/1014; H01L 51/0032; H01L 51/005; H01L 51/0052; H01L 51/0054; H01L 51/0055; H01L 51/0056; H01L 51/0059; H01L 51/006; H01L 51/0062; H01L 51/50; H01L 51/5012; H01L 51/5052; H01L 51/5056; H01L 51/506; H01L 51/5072; H01L 51/5076
USPC ....... 428/690, 691, 411.4, 336, 917; 427/58, 427/66; 313/500–512; 257/40, 88–104, 257/E51.001–E51.052; 252/301.16–301.35; 977/755
See application file for complete search history.

(56) References Cited

U.S. PATENT DOCUMENTS 3,008,897 A  11/1961  Burk, Jr. et al.
5,077,142 A  12/1991  Sakon et al.
(Continued)

FOREIGN PATENT DOCUMENTS

EP  0765106 A2  3/1997
EP  1 061 112 A1  12/2000
(Continued)

OTHER PUBLICATIONS

Patent Abstracts of Japan, JP 3-000790, Jan. 7, 1991.
(Continued)

Primary Examiner — Andrew K Bohaty
(74) Attorney, Agent, or Firm — Oblon, McClelland, Maier & Neustadt, L.L.P.

(57) ABSTRACT

An organic electroluminescence device having a layer of an organic light emitting medium which comprises (A) a specific arylamine compound and (B) at least one compound selected from specific anthracene derivatives, spirofluorene derivatives, compounds having condensed rings and metal complex compounds and is disposed between a pair of electrodes and an organic light emitting medium comprising the above components (A) and (B) are provided. The organic electroluminescence device exhibits a high purity of color, has excellent heat resistance and a long life and efficiently emits bluish to yellowish light. The organic light emitting medium can be advantageously used for the organic electroluminescence device.

11 Claims, No Drawings

Related U.S. Application Data continuation of application No. 13/964,203, filed on Aug. 12, 2013, now Pat. No. 9,728,727, which is a continuation of application No. 13/675,037, filed on Nov. 13, 2012, now abandoned, which is a division of application No. 12/773,307, filed on May 4, 2010, now Pat. No. 8,334,648, which is a continuation of application No. 11/207,933, filed on Aug. 22, 2005, now Pat. No. 7,927,716, which is a division of application No. 10/617,397, filed on Jul. 11, 2003, now Pat. No. 7,651,786.

(51) Int. Cl.

| | |
|---|---|
| *H01L 51/00* | (2006.01) |
| *C07C 13/567* | (2006.01) |
| *C07C 13/72* | (2006.01) |
| *C07C 15/28* | (2006.01) |
| *C07C 15/30* | (2006.01) |
| *C07C 15/38* | (2006.01) |
| *C07C 15/52* | (2006.01) |
| *H05B 33/14* | (2006.01) |
| *H01L 51/50* | (2006.01) |
| *B82Y 30/00* | (2011.01) |
| *H01L 51/52* | (2006.01) |
| *H01L 51/56* | (2006.01) |

(52) U.S. Cl.
CPC ...... *H01L 51/0096* (2013.01); *H01L 51/5012* (2013.01); *H01L 51/5024* (2013.01); *H01L 51/5052* (2013.01); *H01L 51/5206* (2013.01); *H01L 51/5221* (2013.01); *H01L 51/56* (2013.01); *Y10S 428/917* (2013.01); *Y10S 977/755* (2013.01)

(56) References Cited

U.S. PATENT DOCUMENTS

| | | |
|---|---|---|
| 5,153,073 A | 10/1992 | Ohnuma et al. |
| 5,759,444 A | 6/1998 | Enokida et al. |
| 5,840,217 A | 11/1998 | Lupo et al. |
| 5,989,737 A | 11/1999 | Xie et al. |
| 6,203,933 B1 | 3/2001 | Nakaya et al. |
| 6,251,531 B1 | 6/2001 | Enokida et al. |
| 6,416,888 B1 | 7/2002 | Kawamura et al. |
| 6,515,182 B2 | 2/2003 | Hosokawa et al. |
| 6,534,199 B1 | 3/2003 | Hosokawa et al. |
| 6,566,807 B1 | 5/2003 | Fujita et al. |
| 6,582,837 B1 | 6/2003 | Toguchi |
| 6,632,543 B1 | 10/2003 | Kawamura |
| 6,657,084 B2 | 12/2003 | Hosokawa et al. |
| 6,700,058 B2 | 3/2004 | Nelles et al. |
| 6,743,948 B1 | 6/2004 | Hosokawa et al. |
| 6,803,120 B2 | 10/2004 | Fukuoka et al. |
| 6,815,090 B1 | 11/2004 | Tagami et al. |
| 6,818,327 B2 | 11/2004 | Tagami et al. |
| 6,866,947 B1 | 3/2005 | Fukuoka et al. |
| 6,927,237 B2 | 8/2005 | Takahashi |
| 6,927,537 B2 | 8/2005 | Takahashi |
| 6,951,693 B2 | 10/2005 | Hosokawa et al. |
| 7,053,255 B2 | 5/2006 | Ikeda et al. |
| 7,081,550 B2 | 7/2006 | Hosokawa et al. |
| 7,087,322 B2 | 8/2006 | Hosokawa et al. |
| 7,361,796 B2 | 4/2008 | Ikeda et al. |
| 7,651,786 B2 | 1/2010 | Matsuura et al. |
| 7,709,102 B2 | 5/2010 | Hosokawa et al. |
| 7,732,063 B2 | 6/2010 | Matsuura et al. |
| 7,927,716 B2 | 4/2011 | Matsuura et al. |
| 8,324,802 B2 | 12/2012 | Matsuura et al. |
| 8,334,648 B2 | 12/2012 | Matsuura et al. |
| 8,709,613 B2 | 4/2014 | Funahashi |
| 9,343,682 B2* | 5/2016 | Matsuura .............. C07C 13/567 |
| 9,728,727 B2* | 8/2017 | Matsuura .............. C07C 13/567 |
| 9,960,358 B2* | 5/2018 | Matsuura ............. H01L 51/0058 |
| 2002/0022150 A1 | 2/2002 | Toguchi et al. |
| 2002/0028346 A1 | 3/2002 | Shi et al. |
| 2002/0034654 A1 | 3/2002 | Toguchi et al. |
| 2002/0037427 A1 | 3/2002 | Taguchi |
| 2002/0048688 A1 | 4/2002 | Fukuoka et al. |
| 2002/0098379 A1 | 7/2002 | Arakane et al. |
| 2003/0077480 A1 | 4/2003 | Hosokawa et al. |
| 2004/0023060 A1* | 2/2004 | Kim ....................... C07C 13/72 428/690 |
| 2004/0214043 A1 | 10/2004 | Tagami et al. |
| 2004/0229081 A1 | 11/2004 | Arakane et al. |
| 2005/0019606 A1 | 1/2005 | Fukuoka et al. |
| 2005/0038296 A1 | 2/2005 | Hosokawa et al. |
| 2005/0064233 A1 | 3/2005 | Matsuura et al. |
| 2005/0129982 A1 | 6/2005 | Fukuoka et al. |
| 2005/0238921 A1 | 10/2005 | Hosokawa et al. |
| 2006/0024523 A1 | 2/2006 | Tagami et al. |
| 2006/0033421 A1 | 2/2006 | Matsuura et al. |
| 2006/0083947 A1 | 4/2006 | Ikeda et al. |
| 2006/0189828 A1 | 8/2006 | Hosokawa et al. |
| 2006/0257687 A1 | 11/2006 | Hosokawa et al. |
| 2007/0003788 A1 | 1/2007 | Tagami et al. |
| 2007/0134515 A1 | 6/2007 | Fukuoka et al. |
| 2007/0142671 A1 | 6/2007 | Hosokawa et al. |
| 2007/0252511 A1 | 11/2007 | Funahashi |
| 2010/0201255 A1 | 8/2010 | Hosokawa et al. |
| 2010/0270913 A1 | 10/2010 | Matsuura et al. |
| 2015/0287929 A1 | 10/2015 | Matsuura et al. |

FOREIGN PATENT DOCUMENTS

| | | |
|---|---|---|
| EP | 1 138 745 | 10/2001 |
| EP | 1 156 536 | 11/2001 |
| EP | 1 167 488 A1 | 1/2002 |
| EP | 1 182 244 A1 | 2/2002 |
| EP | 1 219 590 | 7/2002 |
| EP | 1 333 018 A1 | 8/2003 |
| EP | 1 347 671 A1 | 9/2003 |
| EP | 1 404 160 | 3/2004 |
| EP | 1 666 561 A1 | 7/2006 |
| EP | 1 757 670 A2 | 2/2007 |
| EP | 1 775 335 A2 | 4/2007 |
| JP | 3-790 | 1/1991 |
| JP | 3-200889 | 9/1991 |
| JP | 04-175395 | 6/1992 |
| JP | 5-21161 A | 1/1993 |
| JP | 7-138561 | 5/1995 |
| JP | 8-12600 | 1/1996 |
| JP | 8-239655 | 9/1996 |
| JP | 10-88122 | 4/1998 |
| JP | 10-95972 A | 4/1998 |
| JP | 10-125467 | 5/1998 |
| JP | 10-125467 A | 5/1998 |
| JP | 11-167992 | 6/1999 |
| JP | 11-236360 A | 8/1999 |
| JP | 11-273860 | 10/1999 |
| JP | 11-338172 A | 12/1999 |
| JP | 2000-196140 | 7/2000 |
| JP | 2000-235893 | 8/2000 |
| JP | 2000-273056 A | 10/2000 |
| JP | 2000-344691 | 12/2000 |
| JP | 2000-344691 A | 12/2000 |
| JP | 2001-052868 | 2/2001 |
| JP | 2001-52870 A | 2/2001 |
| JP | 2001-131541 | 5/2001 |
| JP | 2001-176664 A | 6/2001 |
| JP | 2001-192651 | 7/2001 |
| JP | 2001-196177 A | 7/2001 |
| JP | 2001-207167 | 7/2001 |
| JP | 2001-250690 | 9/2001 |
| JP | 2001-335516 | 12/2001 |
| JP | 2001-338760 A | 12/2001 |
| JP | 2002-50481 A | 2/2002 |
| JP | 2002-198183 | 7/2002 |
| JP | 2002-198183 A | 7/2002 |
| JP | 2007-201491 | 8/2007 |
| JP | 3998903 | 8/2007 |

(56) References Cited

FOREIGN PATENT DOCUMENTS

| WO | WO 99/40655 | 8/1999 |
| --- | --- | --- |
| WO | WO 00/039247 | 7/2000 |
| WO | WO 01/021729 | 3/2001 |
| WO | WO 01/23344 | 4/2001 |
| WO | WO 01/023497 | 4/2001 |
| WO | WO 01/023497 A1 | 4/2001 |
| WO | WO 01/048116 | 7/2001 |
| WO | 2002-080433 | 3/2002 |
| WO | WO 02/020460 | 3/2002 |
| WO | WO 02/20460 A1 | 3/2002 |
| WO | WO 02/038524 | 5/2002 |
| WO | WO 02/052904 | 7/2002 |
| WO | WO 02/052904 A1 | 7/2002 |
| WO | WO 02/102118 | 12/2002 |

OTHER PUBLICATIONS

Patent Abstracts of Japan, JP 2000-273056, Oct. 3, 2000.
Patent Abstracts of Japan, JP 2000-344691, Dec. 12, 2000.
Patent ABstracts of Japan, JP 2002-050481, Feb. 15, 2002.
C.W. Tang, et al., "Organic Electroluminescent Diodes", Received May 12, 1987; accepted for publication Jul. 20, 1987; Appl Phys. Letter 51 (12), Sep. 21, 1987; pp. 913-915.
Patent Abstracts of Japan, JP 08-199162, Aug. 6, 1996.
Japanese Office Action dated Mar. 6, 2012, in Japan Patent application No. 2009-213368.
*Idemitsu Kosan Co., Ltd.*, v. *SFC Co. Ltd.*, No. 2016-2721 (Fed. Cir. Sep. 15, 2017) (affirming Jul. 29, 2016 decision of Patent Trial and Appeal Board finding claims 1-5, 7-11, 13, and 14 of related U.S. Pat. No. 8,334,648 invalid as obvious over WO 02/052904).
Steuber et al., "White Light Emission from Organic LEDs Utilizing Spiro Compounds with High-Temperature Stability", Advanced Materials, vol. 12, No. 2, 2000, pp. 130-133.
George C. Guilbault et al., "Practical Fluorescence", Marcel Dekker, Inc., New York (1973), pp. 86-97.
Moss et al., "Glossary of Class Names of Organic Compounds and Reactive Intermediates Based on Structure", International Union of Pure and Applied Chemistry, vol. 67, Nos. 8/9, 1995, pp. 1307-1314.
Lide, "CRC Handbook of Chemistry and Physics", CRC Press, Inc., 1995, pp. 2-23-2-26.
Petition for Inter Partes Review of U.S. Pat. No. 8,334,648 filed Jan. 14, 2015 in IPR 2015-00564.
Opposition Request by Merck with respect to European Patent No. EP 1 541 657 B2, filed Mar. 22, 2011 (with English translation).
Opposition Request with respect to Korean Patent No. KR 10-1018547, filed Jan. 27, 2012 (with English translation).
Opposition Request by Merck with respect to European Patent No. EP 2 199 361 B9, filed Jul. 19, 2012 (with English translation).
Opposition Request by LG Chem with respect to Taiwan Patent No. I278248, filed Oct. 23, 2009 (with English translation).
Opposition Request by Merck with respect to Taiwan Patent No. I278248, filed Sep. 16, 2009 (with English translation).
Opposition Request by Tae Wha with respect to Taiwan Patent No. I278248, filed Dec. 9, 2011 (with English translation).
PTAB Decision issued in IPR2015-00564 dated Aug. 7, 2015.
PTAB Scheduling Order issued in IPR2015-00564 dated Aug. 7, 2015.
PTAB Final Written Decision issued in IPR2015-00564 dated Jul. 29, 2016.
Case No. IPR2015-00564-012—Idemitsu—Patent Owner Response—IPR2015-00564-110915.
Petitioner's Reply to Patent Owner Response filed in IPR 2015-00564 on Feb. 8, 2016.

* cited by examiner

ORGANIC ELECTROLUMINESCENCE DEVICE AND ORGANIC LIGHT EMITTING MEDIUM

RELATED APPLICATIONS

This application is a continuation of U.S. application Ser. No. 15/638,805, filed Jun. 30, 2017, which is a continuation of U.S. application Ser. No. 13/964,203, filed Aug. 12, 2013, now U.S. Pat. No. 9,728,727; which is a continuation of U.S. application Ser. No. 13/675,037, filed Nov. 13, 2012, now abandoned; which is a division of application Ser. No. 12/773,307, filed May 4, 2010, now U.S. Pat. No. 8,334,648; which is a continuation of application Ser. No. 11/207,933, filed Aug. 22, 2005, now U.S. Pat. No. 7,927,716, which is a division of application Ser. No. 10/617,397, filed Jul. 11, 2003, now U.S. Pat. No. 7,651,786. Priority to Japan 2002-211308, filed Jul. 19, 2002, is claimed, and all are incorporated herein by reference.

TECHNICAL FIELD

The present invention relates to an organic electroluminescence ("electroluminescence" will be referred to as "EL", hereinafter) device and an organic light emitting medium, and more particularly, to an organic EL device which exhibits excellent purity of color, has excellent heat resistance and a long life and efficiently emits bluish to yellowish light and an organic light emitting medium which is advantageously used for the organic EL device.

BACKGROUND ART

An organic EL is a spontaneous light emitting device which utilizes the principle that a fluorescent substance emits light by energy of recombination of holes injected from an anode and electrons injected from a cathode when an electric field is applied.

Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials.

Tang et al used a laminate structure using tris(8-hydroxy-quinolinato)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased and that excited particles formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material, chelate complexes such as tris(8-quinolinato)aluminum, coumarine derivatives, tetraphenyl-butadiene derivatives, bisstyrylarylene derivatives and oxadiazole derivatives are known. It is reported that light in the visible region ranging from blue light to red light can be obtained by using these light emitting materials and development of a device exhibiting color images is expected (For example, Japanese Patent Application Laid-Open Nos. Heisei 8(1996)-239655, Heisei 7(1995)-138561 and Heisei 3(1991)-200289).

Devices using bisanthracene derivatives as the hole transporting material or the light emitting material are disclosed in the U.S. Pat. No. 3,008,897 and Japanese Patent Application Laid-Open No. Heisei 8(1996)-12600. Although bisanthracene derivatives can be used as the material emitting blue light, the efficiency of light emission and the life are insufficient for practical applications. In Japanese Patent Application Laid-Open No. 2001-207167, a device using an aminoanthracene derivative as the material emitting green light is disclosed. However, the organic EL device using this material cannot be used for the practical applications since the device has poor heat resistance due to the low glass transition temperature of the material and light emission of a long life and a high efficiency cannot be obtained. Other organic devices of a long life and excellent properties are recently reported. However, the life and the properties are not always sufficient. Therefore, the development of an organic EL device exhibiting more excellent properties have been strongly desired.

DISCLOSURE OF THE INVENTION

Under the above circumstances, the present invention has an object of providing an organic EL device which exhibits a high purity of color, has excellent heat resistance and a long life and efficiently emits bluish to yellowish light and an organic light emitting medium which can be advantageously used for the organic EL device.

As the result of extensive studies by the present inventors to achieve the above object, it was found that, when an organic light emitting medium comprised a combination of a specific arylamine compound and at least one compound selected from specific anthracene derivatives, spirofluorene derivatives, compounds having condensed rings and metal complex compounds and an organic electroluminescence device had a layer of the medium disposed between a pair of electrodes, the organic EL device exhibited a high purity of color, had excellent heat resistance and a long life and efficiently emitted bluish to yellowish light. The present invention has been completed based on this knowledge.

The present invention provides an electroluminescence device comprising a pair of electrodes and a layer of an organic light emitting medium disposed between the pair of electrodes, wherein the layer of an organic light emitting medium comprises:

(A) at least one compound selected from substituted and unsubstituted arylamines having 10 to 100 carbon atoms, and (B) at least one compound selected from:
anthracene derivatives represented by following general formula (I):

$$A^1\text{-}L\text{-}A^2 \qquad (I)$$

wherein $A^1$ and $A^2$ each independently represent a substituted or unsubstituted monophenylanthryl group or a substituted or unsubstituted diphenylanthryl group and may represent a same group or different groups, and L represents a single bond or a divalent bonding group,
anthracene derivatives represented by following general formula (II):

$$A^3\text{-}An\text{-}A^4 \qquad (II)$$

wherein $Ar^1$ represents a substituted or unsubstituted divalent anthracene residue group, $A^3$ and $A^4$ each independently represent a substituted or unsubstituted aryl group having 6 to 40 carbon atoms, at least one of $A^3$ and $A^4$ represents a substituted or unsubstituted monovalent condensed aromatic ring group or a substituted or unsubstituted aryl group having 10 or more carbon atoms, and $A^3$ and $A^4$ may represent a same group or different groups, spirofluorene derivatives represented by following general formula (III):

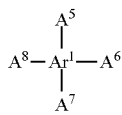

wherein $Ar^1$ represents a substituted or unsubstituted spirofluorene residue group, $A^5$ to $A^8$ each independently represent a substituted or unsubstituted aryl group having 6 to 40 carbon atoms, compounds having condensed rings represented by following general formula (IV):

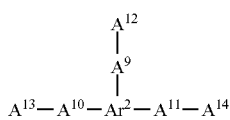

wherein $Ar^2$ represents a substituted or unsubstituted aromatic ring group having 6 to 40 carbon atoms, $A^9$ to $A^{11}$ each independently represent a substituted or unsubstituted arylene group having 6 to 40 carbon atoms, $A^{12}$ to $A^{14}$ each independently represent hydrogen atom, an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, an arylamino group having 5 to 16 carbon atoms, nitro group, cyano group, an ester group having 1 to 6 carbon atoms or a halogen atom, and at least one of $A^9$ to $A^{14}$ represents a group having condensed aromatic rings, and metal complex compounds. The present invention also provides an electroluminescence device described above, wherein component (B) is at least one compound selected from the anthracene derivatives represented by general formulae (I) and (II) shown above.

The present invention provides an organic light emitting medium which comprises (A) at least one compound selected from substituted and unsubstituted arylamines having 10 to 100 carbon atoms and (B) at least one compound selected from anthracene derivatives represented by general formula (I) shown above, anthracene derivatives represented by following general formula (II) shown above, spirofluorene derivatives represented by general formula (III) shown above, compounds having condensed rings represented by general formula (IV) shown above and metal complex compounds described above. The present invention also provides an organic light emitting medium described above, wherein component (B) is at least one compound selected from the anthracene derivatives represented by general formulae (I) and (II) shown above.

THE MOST PREFERRED EMBODIMENT TO CARRY OUT THE INVENTION

The organic EL device of the present invention is a device having a structure comprising a pair of electrodes and a layer of an organic light emitting medium disposed between the pair of electrodes.

In the present invention, an organic light emitting medium comprising a combination of (A) at least one compound selected from substituted and unsubstituted arylamine compounds having 10 to 100 carbon atoms and (B) at least one compound selected from the anthracene derivatives represented by the above general formula (I), the anthracene derivatives represented by the above general formula (II), the spirofluorene derivatives represented by the above general formula (III), the compounds having condensed rings represented by the above general formula (IV) and the above metal complex compounds, is used in the layer of an organic light emitting medium.

Examples of the arylamine compound of component (A) include arylamine compounds represented by the following general formula (V):

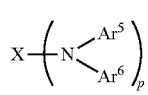

wherein $X^3$ represents a substituted or unsubstituted condensed aromatic ring group having 10 to 40 nuclear carbon atoms, $Ar^5$ and $Ar^6$ each independently represent a substituted or unsubstituted monovalent aromatic group having 6 to 40 carbon atoms, and p represents an integer of 1 to 4.

In general formula (V), examples of the group represented by $X^3$ include residue groups derived from naphthalene, phenanthrene, fluoranthene, anthracene, pyrene, perylene, coronene, chrysene, picene, diphenylanthracene, fluorene, triphenylene, rubicene, benzoanthracene, phenylanthracene, bisanthracene, dianthracenylbenzene and dibenzoanthracene. Among these groups, residue groups derived from chrysene, pyrene and anthracene are preferable.

Examples of the monovalent aromatic group having 6 to 40 carbon atoms which is represented by $Ar^5$ and $Ar^6$ include phenyl group, naphthyl group, anthranyl group, phenanthryl group, pyrenyl group, coronyl group, biphenyl group, terphenyl group, fluorenyl group, furanyl group, thienyl group, benzothienyl group, indolyl group and carbazolyl group. Among these groups, phenyl group, naphthyl group, pyrenyl group and biphenyl group are preferable.

As the arylamine compound represented by general formula (V), arylamine compounds represented by the following general formula (V-a):

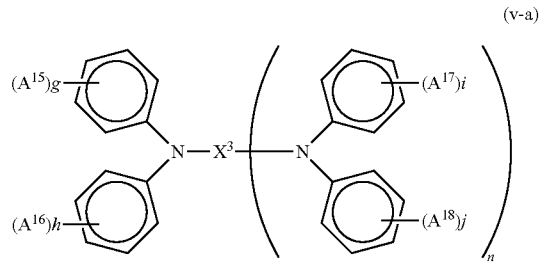

wherein X³ is as defined in general formula (V), are preferable.

In the above general formula (V-a), Ar¹⁵ to Ar¹⁸ each independently represent hydrogen atom, a substituted or unsubstituted alkyl group having 1 to 50 carbon atoms and preferably 1 to 20 carbon atoms, a substituted or unsubstituted aryl group having 5 to 50 carbon atoms and preferably 5 to 20 carbon atoms, a substituted or unsubstituted aralkyl group having 7 to 50 carbon atoms and preferably 7 to 40 carbon atoms, a substituted or unsubstituted cycloalkyl group having 3 to 50 carbon atoms and preferably 5 to 12 carbon atoms, a substituted or unsubstituted alkoxyl group having 1 to 50 carbon atoms and preferably 1 to 6 carbon atoms, a substituted or unsubstituted aryloxyl group having 5 to 50 carbon atoms and preferably 5 to 18 carbon atoms, a substituted or unsubstituted arylamino group having 5 to 50 carbon atoms and preferably 5 to 18 carbon atoms or a substituted or unsubstituted alkylamino group having 1 to 20 carbon atoms and preferably 1 to 6 carbon atoms.

Examples of the substituted or unsubstituted alkyl group represented by Ar¹⁵ to Ar¹⁸ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group and α-benzyloxybenzyl group.

Examples of the substituted or unsubstituted aryl group represented by Ar¹⁵ to Ar¹⁸ include phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group and pyrenyl group.

Examples of the substituted or unsubstituted aralkyl group represented by Ar¹⁵ to Ar¹⁸ include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

Examples of the substituted or unsubstituted cycloalkyl group represented by Ar¹⁵ to Ar¹⁸ include cyclopropyl group, cyclobutyl group, cyclopentyl group and cyclohexyl group.

Examples of the substituted or unsubstituted alkoxyl group represented by Ar¹⁵ to Ar¹⁸ include methoxyl group, ethoxyl group, propoxyl group, isopropoxyl group, butoxyl group, isobutoxyl group, sec-butoxyl group, tert-butoxyl group, various types of pentyloxyl groups and various types of hexyloxyl groups.

Examples of the substituted or unsubstituted aryloxyl group represented by Ar¹⁵ to Ar¹⁸ include phenoxyl group, tolyloxyl group and naphthyloxyl group.

Examples of the substituted or unsubstituted arylamino group represented by Ar¹⁵ to Ar¹⁸ include diphenylamino group, ditolylamino group, dinaphthylamino group and naphthylphenylamino group.

Examples of the substituted or unsubstituted alkylamino group represented by Ar¹⁵ to Ar¹⁸ include dimethylamino group, diethylamino group and dihexylamino group.

In general formula (V-a), g, h, i and j each represent an integer of 0 to 5 and preferably an integer of 0 to 2. Atoms and groups represented by a plurality of Ar¹⁵ to Ar¹⁸ may be the same with or different from each other and may be bonded to each other to form a saturated or unsaturated ring when g, h, i and j each represent an integer of 2 or greater. n represents an integer of 0 to 3. At least one of Ar¹⁵ to Ar¹⁸ represents a substituted or unsubstituted secondary or tertiary alkyl group having 3 to 10 carbon atoms. Examples of the secondary or tertiary alkyl group include the secondary and tertiary alkyl groups among the groups described as the examples of the alkyl group represented by Ar¹⁵ to Ar¹⁸.

As the arylamine compound represented by general formula (V), arylamine compounds represented by the following general formula (V-b):

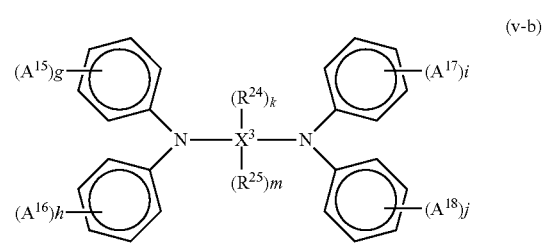

wherein X³, Ar¹⁵ to Ar¹⁸, g, h, i and j are as defined in general formula (V-a), and atoms and groups represented by a plurality of Ar¹⁵ to Ar¹⁸ may be the same with or different from each other and may be bonded to each other to form a saturated or unsaturated ring when g, h, i and j each represent an integer of 2 or greater, are also preferable.

In general formula (V-b), R²⁴ and R²⁵ each independently represent hydrogen atom, a substituted or unsubstituted alkyl group having 1 to 10 carbon atoms and preferably 1 to 6 carbon atoms, a substituted or unsubstituted aryl group having 6 to 20 carbon atoms and preferably 6 to 14 carbon atoms, a substituted or unsubstituted aralkyl group having 7 to 50 carbon atoms and preferably 7 to 40 carbon atoms, a substituted or unsubstituted alkoxyl group having 1 to 50 carbon atoms and preferably 1 to 6 carbon atoms or a substituted or unsubstituted aryloxyl group having 5 to 50 carbon atoms and preferably 5 to 18 carbon atoms.

Examples of the groups represented by R²⁴ and R²⁵ include the groups in which the number of carbon atoms is within the above range among the groups described as the examples of the groups represented by Ar¹⁵ to Ar¹⁸.

At least one of R²⁴ and R²⁵ represents a substituted or unsubstituted secondary or tertiary alkyl group having 3 to 10 carbon atoms. Examples of the secondary or tertiary alkyl group include the secondary and tertiary alkyl groups among the groups described as the examples of the alkyl group represented by Ar¹⁵ to Ar¹⁸.

In general formula (V-b), k and m each represent an integer of 0 to 2.

In the present invention, the arylamine compound of component (A) may be used singly or in combination of two or more.

Examples of the substituent in the compounds represented by general formulae (V), (V-a) and (V-b) include alkyl groups having 1 to 6 carbon atoms, cycloalkyl groups having 3 to 6 carbon atoms, alkoxyl groups having 1 to 6 carbon atoms, aryloxyl groups having 5 to 18 carbon atoms, aralkyloxyl groups having 7 to 18 carbon atoms, arylamino groups having 5 to 16 carbon atoms, nitro group, cyano group, ester groups having 1 to 6 carbon atoms and halogen atoms. Examples of the above groups and atoms include the atoms and groups described as the examples of the atoms and the groups represented by $A^{12}$ to $A^{14}$ in general formula (IV) described in the following.

In the present invention, the compound of component (B) is at least one compound selected from [1] anthracene derivatives represented by the following general formula (I), [2] anthracene derivatives represented by the following general formula (II), [3] spirofluorene derivatives represented by the following general formula (III), [4] compounds having condensed rings represented by the following general formula (IV) and [5] metal complex compounds shown in the following.

It is preferable that the compound of component (B) is at least one compound selected from the anthracene derivatives represented by general formulae (I) and (II).

[1] Anthracene Derivatives Represented by General Formula (I):

wherein $A^1$ and $A^2$ each independently represent a substituted or unsubstituted monophenylanthryl group or a substituted or unsubstituted diphenylanthryl group and may represent the same group or different groups, and L represents a single bond or a divalent bonding group.

As the anthracene derivative represented by general formula (I), anthracene derivatives represented by the following general formula (I-a) and anthracene derivatives represented by the following general formula (I-b) are preferable.

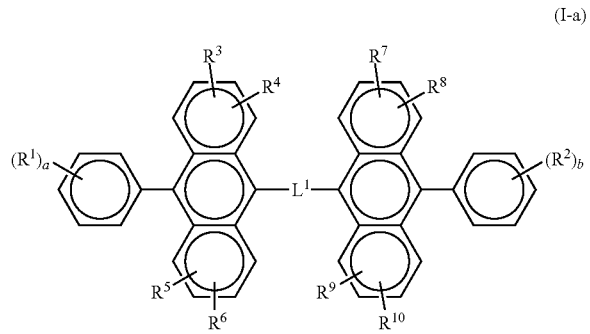

In the above general formula (I-a), $R^1$ to $R^{10}$ each independently represent hydrogen atom, an alkyl group, a cycloalkyl group, an aryl group which may be substituted, an alkoxyl group, an aryloxyl group, an alkylamino group, an alkenyl group, an arylamino group or a heterocyclic group which may be substituted, a and b each represent an integer of 1 to 5, atoms or groups represented by a plurality of $R^1$ and $R^2$ may be the same with or different from each other and may be bonded to each other to form a ring when a and b each represent an integer of 2 or greater, groups represented by combinations of $R^3$ and $R^4$, $R^5$ and $R^6$, $R^7$ and $R^8$, and $R^9$ and $R^{10}$ may be bonded to each other to form a ring, and $L^1$ represents a single bond, —O—, —S—, —N(R)— (R representing an alkyl group or an aryl group which may be substituted), an alkylene group or an arylene group.

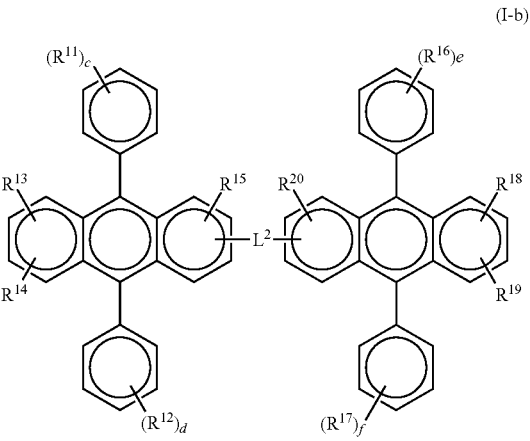

In the above general formula (I-b), $R^{11}$ to $R^{20}$ each independently represent hydrogen atom, an alkyl group, a cycloalkyl group, an aryl group which may be substituted, an alkoxyl group, an aryloxyl group, an alkylamino group, an arylamino group or a heterocyclic group which may be substituted, c, d, e and f each represent an integer of 1 to 5, atoms or groups represented by a plurality of $R^{11}$, $R^{12}$, $R^{16}$ and $R^{17}$ may be the same with or different from each other and may be bonded to each other to form a ring when c, d, e and f each represent an integer of 2 or greater, groups represented by combinations of $R^{13}$ and $R^{14}$, and $R^{18}$ and $R^{19}$ may be bonded to each other to form a ring, and $L^2$ represents a single bond, —O—, —S—, —N(R)— (R representing an alkyl group or an aryl group which may be substituted), an alkylene group or an arylene group.

That a group may be substituted means the group is substituted or unsubstituted.

In the above general formulae (I-a) and (I-b), among the groups represented by $R^1$ to $R^{20}$, alkyl groups having 1 to 6 carbon atoms, cycloalkyl groups having 3 to 6 carbon atoms, aryl groups having 5 to 18 carbon atoms, alkoxyl groups having 1 to 6 carbon atoms, aryloxyl groups having 5 to 18 carbon atoms and alkenyl groups having 1 to 6 carbon atoms are preferable; amino groups substituted with an aryl group having 5 to 16 carbon atoms are preferable as the arylamino group; and triazole group oxadiazole group, quinoxaline group, furanyl group and thienyl group are preferable as the heterocyclic groups.

As the alkyl group represented by R in —N(R)— which is represented by $L^1$ and $L^2$, alkyl groups having 1 to 6 carbon atoms, alkylene groups having 1 to 20 carbon atoms and aryl groups having 5 to 18 carbon atoms are preferable.

[2] Anthracene Derivatives Represented by General Formula (II):

wherein An represents a substituted or unsubstituted divalent anthracene residue group, $A^3$ and $A^4$ each independently represent a substituted or unsubstituted aryl group having 6 to 40 carbon atoms, at least one of $A^3$ and $A^4$ represents a substituted or unsubstituted monovalent condensed aromatic ring or a substituted or unsubstituted aryl group having 10 or more carbon atoms, and $A^3$ and $A^4$ may represent the same group or different groups.

Examples of the aryl group represented by $A^3$ and $A^4$ include phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group and condensed aromatic ring groups which are residue groups derived from naphthalene, phenanthrene, fluoranthene, anthracene, pyrene, perylene, coronene, chrysene, picene, fluorene, terphenyl, diphenylanthracene, biphenyl, carbazole, triphenylene, rubicene, benzoanthracene, phenylanthracene, bisanthracene, dianthracenylbenzene and dibenzoanthracene, which may be substituted or unsubstituted.

As the anthracene derivative represented by the above general formula (II), anthracene derivatives represented by the following general formula (II-a):

$$X^1\text{-An-}X^2 \quad \quad \quad \text{(II-a)}$$

wherein $Ar^1$ represents a substituted or unsubstituted divalent anthracene residue group and $X^1$ and $X^2$ each independently represent a monovalent residue group derived from naphthalene, phenanthrene, fluoranthene, anthracene, pyrene, perylene, coronene, chrysene, picene, diphenylanthracene, carbazole, triphenylene, rubicene, benzoanthracene, phenylanthracene, bisanthracene, dianthracenylbenzene or dibenzoanthracene, which may be substituted or unsubstituted, are preferable.

[3] Spirofluorene Derivatives Represented by General Formula (III):

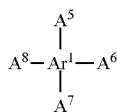

wherein $Ar^1$ represents a substituted or unsubstituted spirofluorene residue group, $A^5$ to $A^8$ each independently represent a substituted or unsubstituted aryl group having 6 to 40 carbon atoms.

Examples of the substituted or unsubstituted aryl group represented by $A^5$ to $A^8$ in the above general formula (III) include phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group and pyrenyl group.

As the spirofluorene derivative represented by the above general formula (III), spirofluorene derivatives represented by the following general formula (III-a):

(III-a)

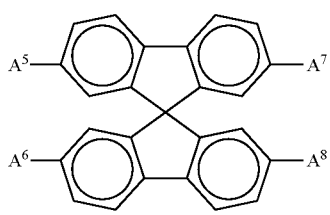

wherein $A^5$ to $A^8$ each independently represent a substituted or unsubstituted biphenyl group or a substituted or unsubstituted naphthyl group, are preferable.

[4] Compounds Having Condensed Rings Represented by General Formula (IV):

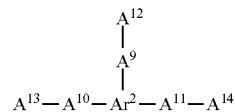

wherein $Ar^2$ represents a substituted or unsubstituted aromatic ring group having 6 to 40 carbon atoms, $A^9$ to $A^{11}$ each independently represent a substituted or unsubstituted arylene group having 6 to 40 carbon atoms, $A^{12}$ to $A^{14}$ each independently represent hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxyl group having 7 to 18 carbon atoms, an arylamino group having 5 to 16 carbon atoms, nitro group, cyano group, an ester group having 1 to 6 carbon atoms or a halogen atom, and at least one of $A^9$ to $A^{14}$ represents a group having condensed aromatic rings.

Examples of the aromatic ring group represented by $Ar^2$ include residue groups derived from benzene, biphenyl, terphenyl, phenanthrene, fluoranthene, anthracene, pyrene, perylene, coronene, chrysene, picene, fluorene, carbazole, rubicene, benzoanthracene and dibenzoanthracene.

Examples of the arylene group represented by $A^9$ to $A^{11}$ include divalent residue groups derived from the aromatic compounds described above as the examples of the aromatic ring group represented by $Ar^2$.

Examples of the alkyl group having 1 to 6 carbon atoms represented by $A^{12}$ to $A^{14}$ include methyl group, ethyl group, propyl group, isopropyl group, butyl group, isobutyl group, sec-butyl group, tert-butyl group, various types of pentyl group and various types of hexyl group.

Examples of the cycloalkyl group having 3 to 6 carbon atoms represented by $A^{12}$ to $A^{14}$ include cyclopropyl group, cyclobutyl group, cyclopentyl group and cyclohexyl group.

Examples of the alkoxyl group having 1 to 6 carbon atoms represented by $A^{12}$ to $A^{14}$ include methoxyl group, ethoxyl group, propoxyl group, isopropoxyl group, butoxyl group, isobutoxyl group, sec-butoxyl group, tert-butoxyl group, various types of pentyloxyl groups and various types of hexyloxyl groups.

Examples of the aryloxyl group having 5 to 18 carbon atoms represented by $A^{12}$ to $A^{14}$ include phenoxyl group, tolyloxyl group and naphthyloxyl group.

Examples of the aralkyloxyl group having 7 to 18 carbon atoms represented by $A^{12}$ to $A^{14}$ include benzyloxyl group, phenetyloxyl group and naphthylmethoxyl group.

Examples of the arylamino group having 5 to 16 carbon atoms represented by $A^{12}$ to $A^{14}$ include diphenylamino group, ditolylamino group, dinaphthylamino group and naphthylphenylamino group.

Examples of the ester group having 1 to 6 carbon atoms represented by $A^{12}$ to $A^{14}$ include methoxycarbonyl group, ethoxycarbonyl group, propoxycarbonyl group and isopropoxycarbonyl group.

Examples of the halogen atoms represented by $A^{12}$ to $A^{14}$ include fluorine atom, chlorine atom and bromine atom. The aryl group in the present invention includes styrylphenyl group, styrylbiphenyl group and styrylnaphthyl group.

As the compound having condensed rings represented by general formula (IV), compounds having condensed rings represented by the following general formula (IV-a):

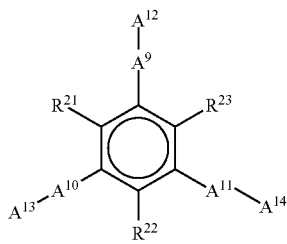

(Iv-a)

wherein $A^9$ to $A^{14}$ are as defined above, $R^{21}$ to $R^{23}$ each independently represent hydrogen atom, an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, an arylamino group having 5 to 16 carbon atoms, nitro group, cyano group, an ester group having 1 to 6 carbon atoms or a halogen atom, and at least one of $A^9$ to $A^{14}$ represents a group having condensed aromatic rings having at least 3 rings, are preferable.

Examples of the groups represented by $R^{21}$ to $R^{23}$ include the groups described as the examples of the groups represented by $A^{12}$ to $A^{14}$ in general formula (IV).

Examples of the substituent in the compounds represented by the above general formulae (I) to (IV), (I-a), (I-b), (II-a), (III-a) and (IV-a) include alkyl groups having 1 to 6 carbon atoms, cycloalkyl groups having 3 to 6 carbon atoms, alkoxyl groups having 1 to 6 carbon atoms, aryloxyl groups having 5 to 18 carbon atoms, aralkyloxyl groups having 7 to 18 carbon atoms, arylamino groups having 5 to 16 carbon atoms, nitro group, cyano group, ester groups having 1 to 6 carbon atoms and halogen atoms. Specific examples of the above substituent include the substituents described as the examples of the substituents for the groups represented by $A^{12}$ to $A^{14}$ in the above general formula (IV).

[5] Metal Complex Compounds

Examples of the metal complex compound described above include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)-aluminum, tris(8-hydroxyquinolinato)gallium, bis(10-hydroxybenzo[h]-quinolinato)beryllium, bis(l O-hydroxybenzo[h]quinolinato)zinc, bis(2-methyl-8-hydroxyquinolinato)chlorogallium, bis(2-methyl-8-hydroxy-quinolinato)(o-cresolato)gallium, bis(2-methyl-8-hydroxyquinolinato)-(1-naphtholato)aluminum and bis(2-methyl-8-hydroxyquinolinato)-(2-naphtholate)gallium. Among these compounds, aluminum chelate complex compounds such as tris(8-hydroxyquinolinato)aluminum, tris(2-methyl-8-hydroxyquinolinato)aluminum and bis(2-methyl-8-hydroxyquinolinato)(1-naphtholato)aluminum are preferable.

In the present invention, the anthracene derivative of component (B) may be used singly or in combination of two or more.

Specific examples of the anthracene derivative represented by the above general formula (I-a) are shown in the following.

EM1

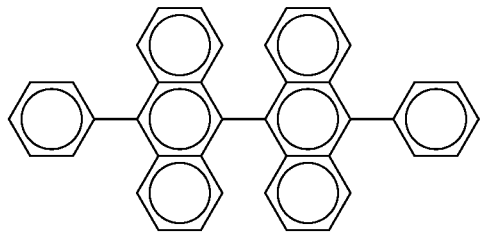

EM2

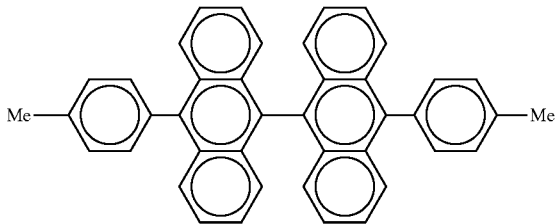

(Me: methyl group; similarly in the following formulae)

EM3

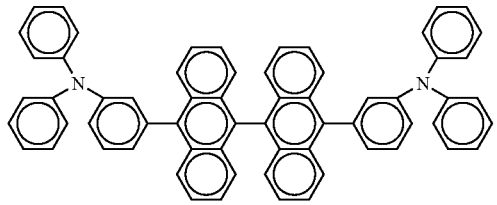

EM4

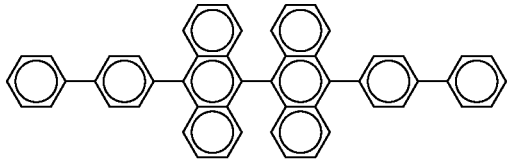

EM5

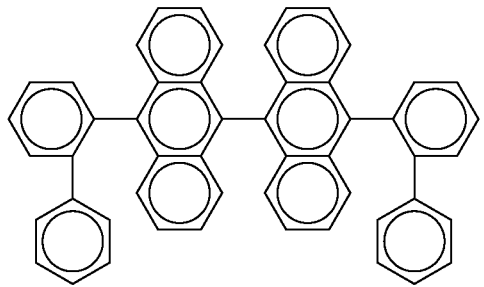

EM6

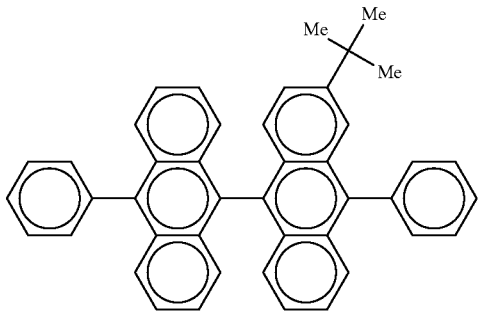

-continued
EM7
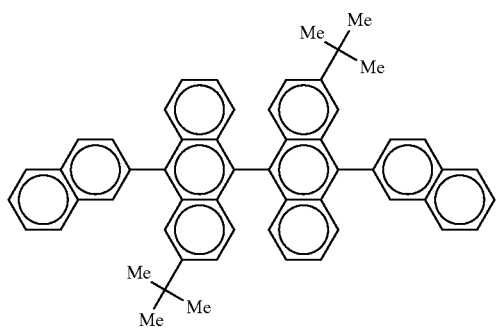
EM8
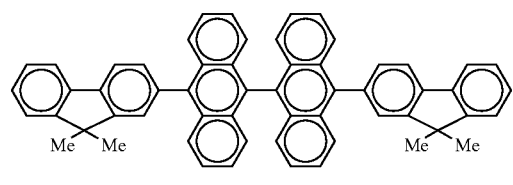
EM9
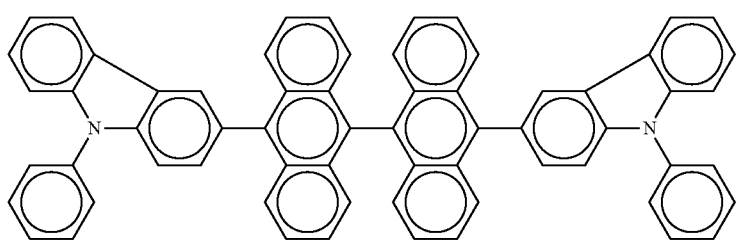
EM10
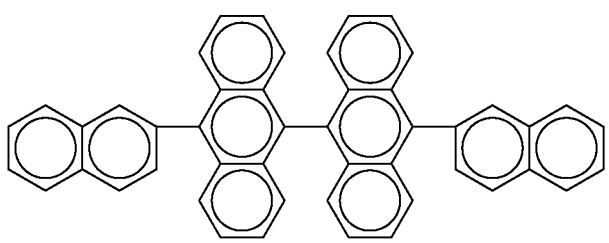
EM11
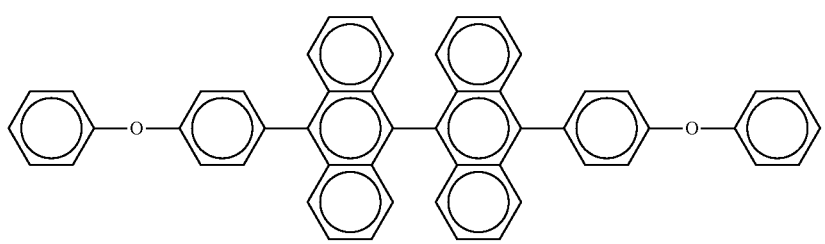
EM12
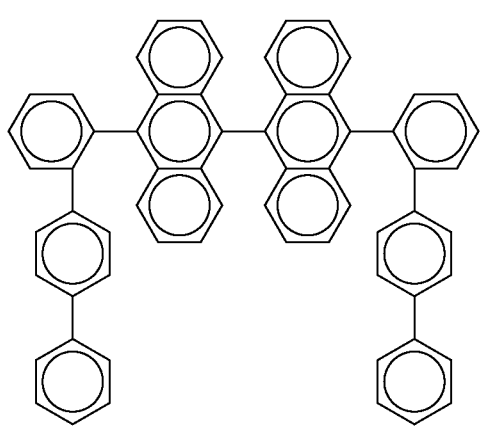

-continued
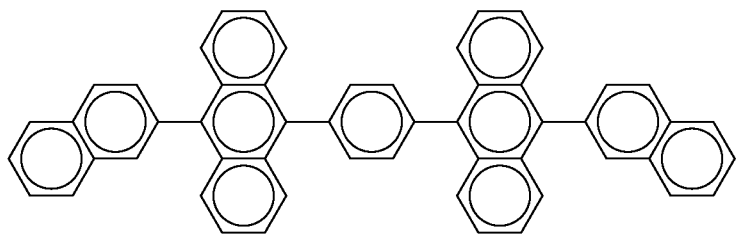
EM13
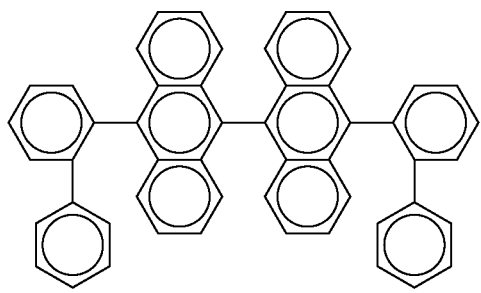
EM14
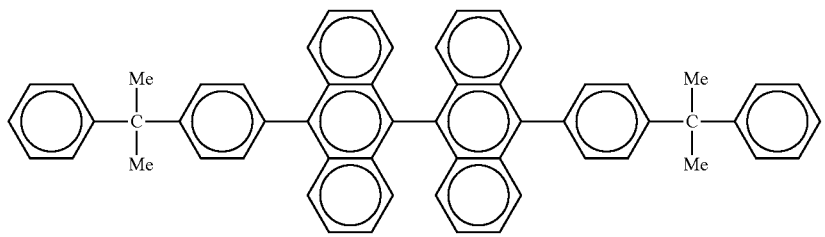
EM15
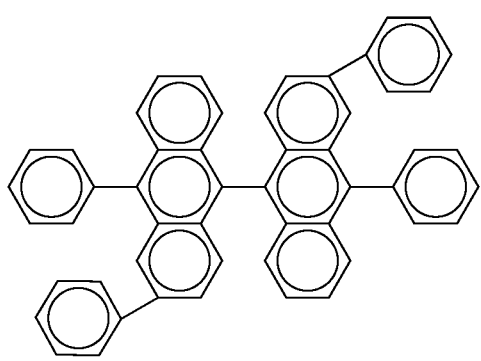
EM16

Specific examples of the anthracene derivative represented by the above general formula (I-b) are shown in the following.
EM17
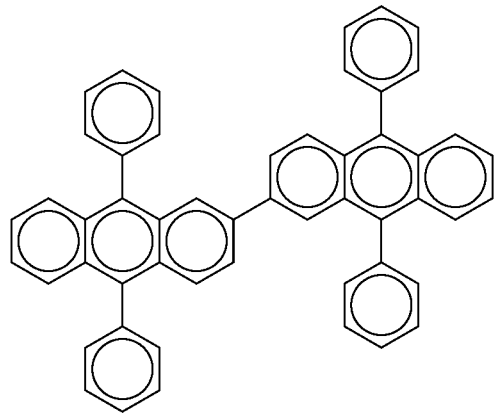
EM18
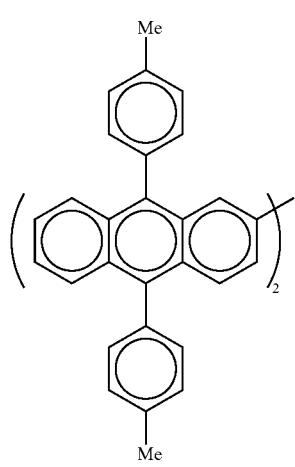
EM19
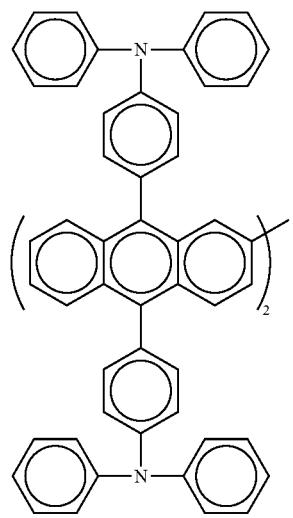
EM20
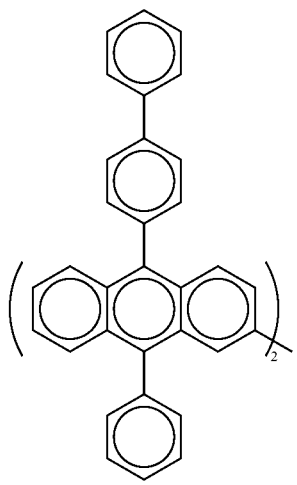
EM21
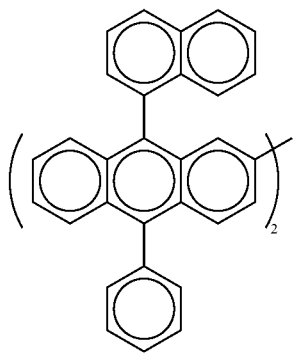
EM22
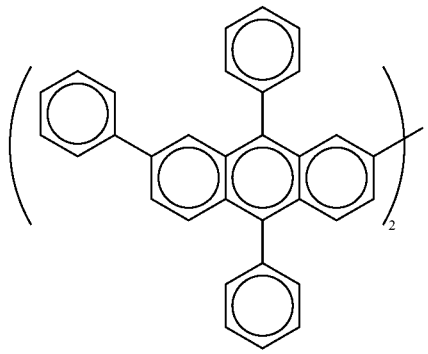
EM23
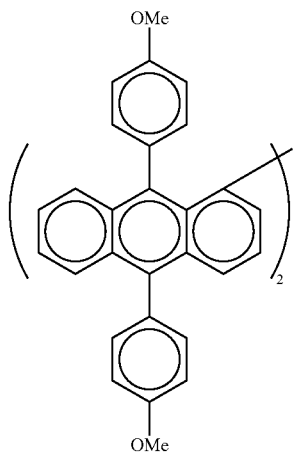

EM24
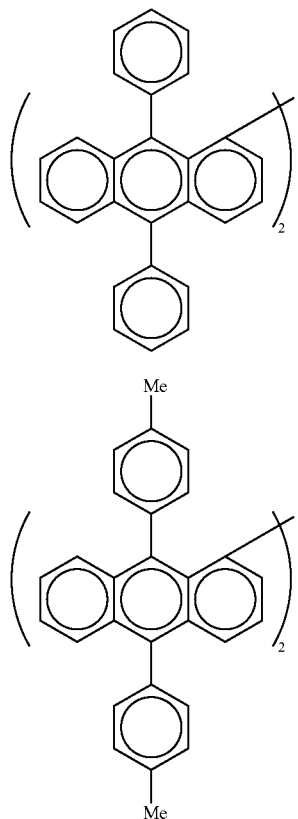
EM25
EM26
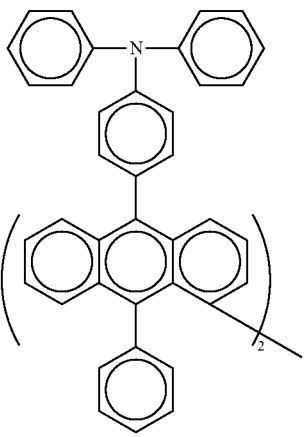
Specific examples of the anthracene derivatives represented by the above general formula (II-a) are shown in the following.
EM27
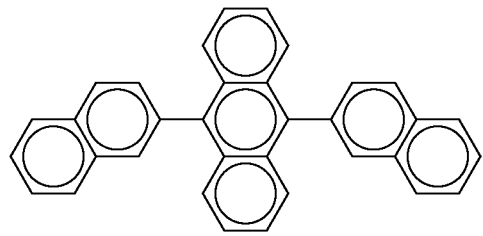
EM28
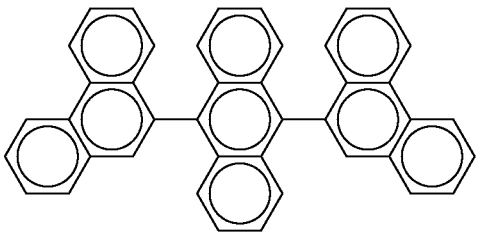
EM29
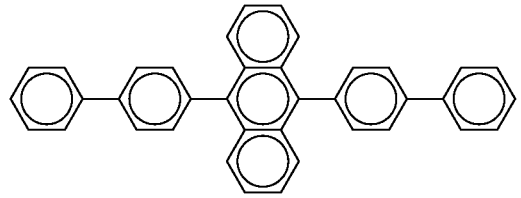
EM30
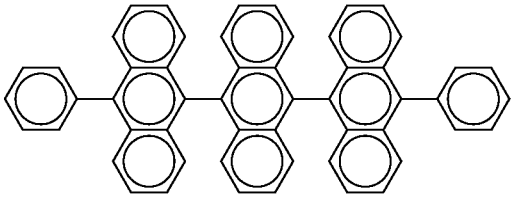

-continued
EM31
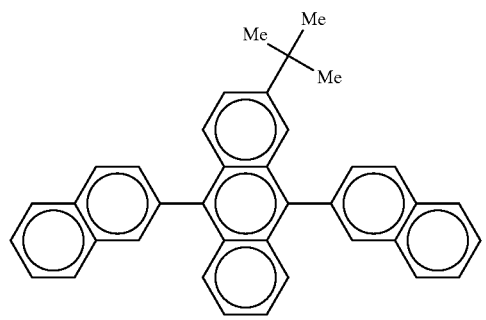
EM32
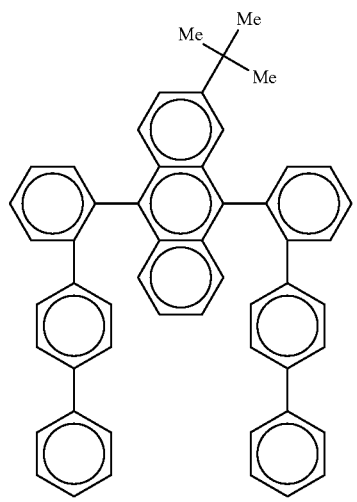
EM33
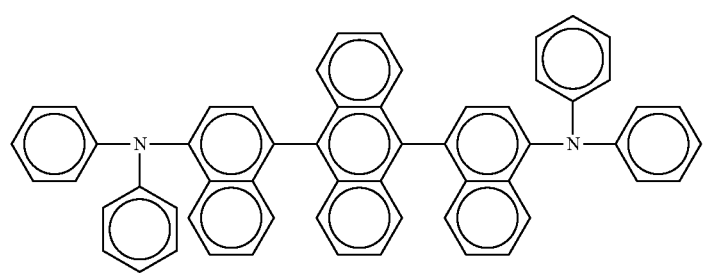
EM34
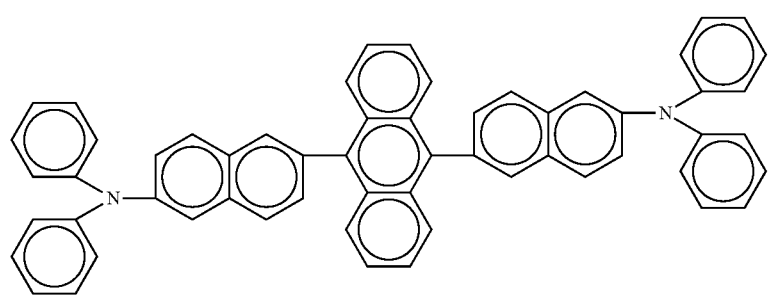
EM35
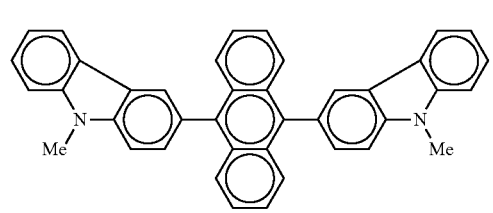
EM36
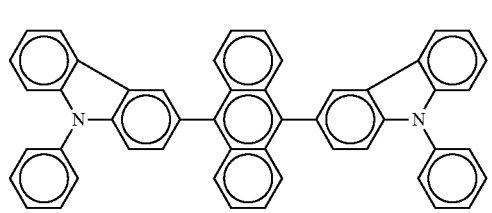
EM37
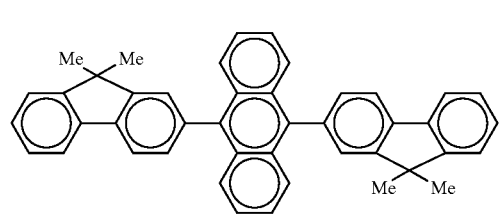
EM38
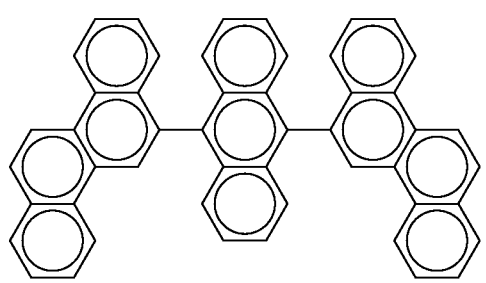

-continued
EM39
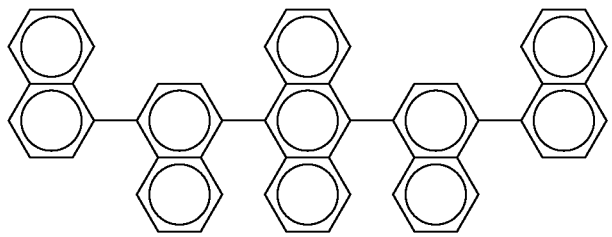
EM40
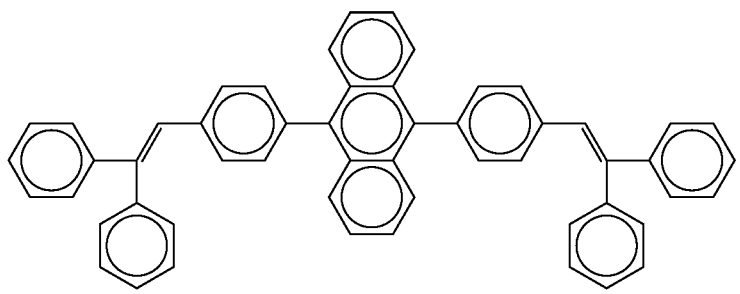
EM41
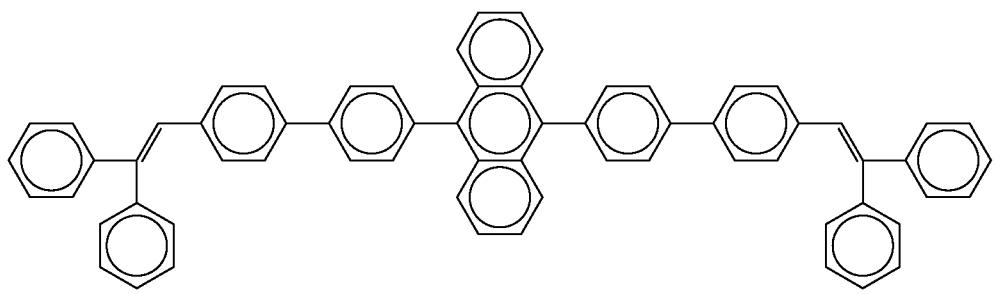
Specific examples of the spirofluorene derivative represented by the above general formula (III-a) are shown in the following.
EM42
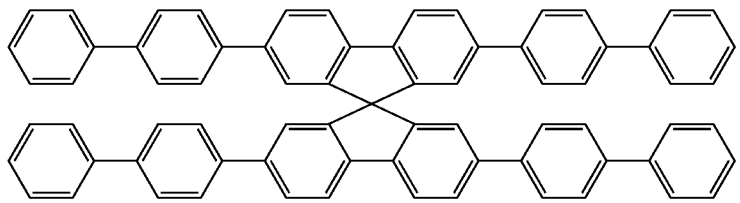
EM43
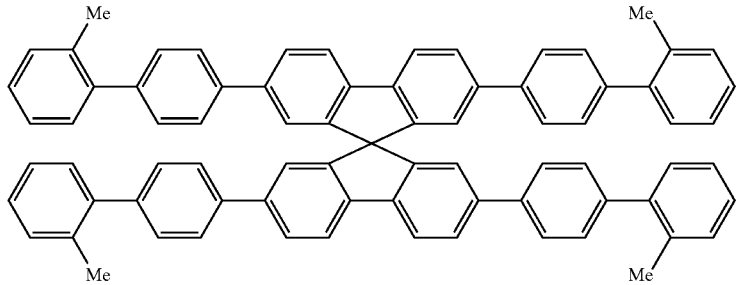

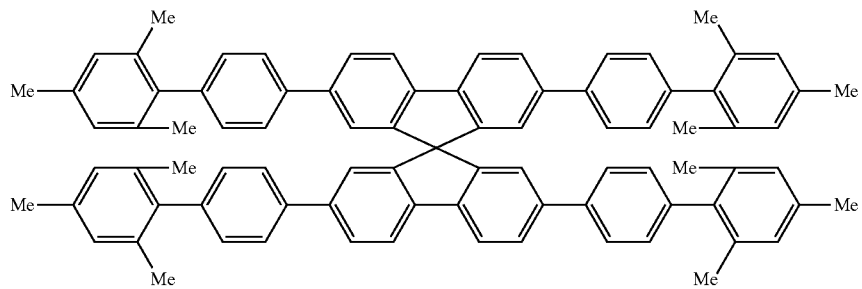
EM44
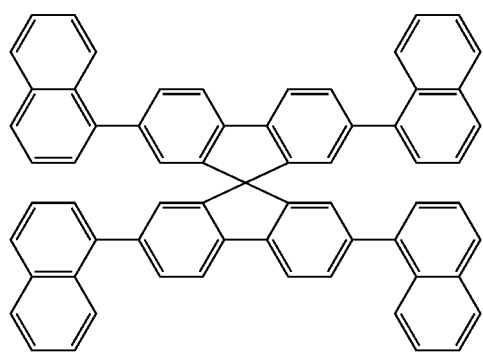
EM45
Specific examples of the compound having condensed rings represented by the above general formula (IV-a) are shown in the following.
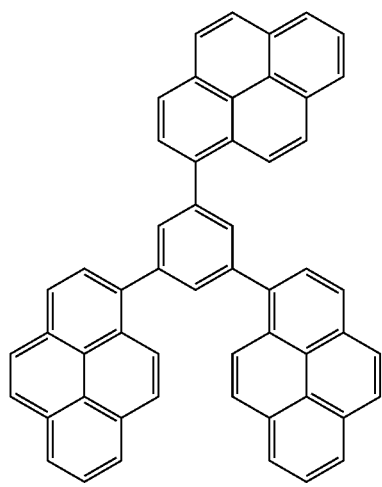
EM46
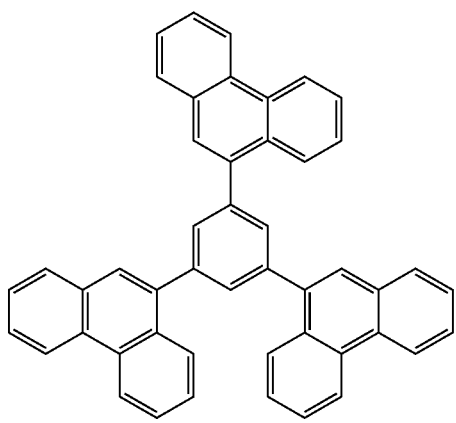
EM47

-continued

EM48

EM49

EM50

-continued
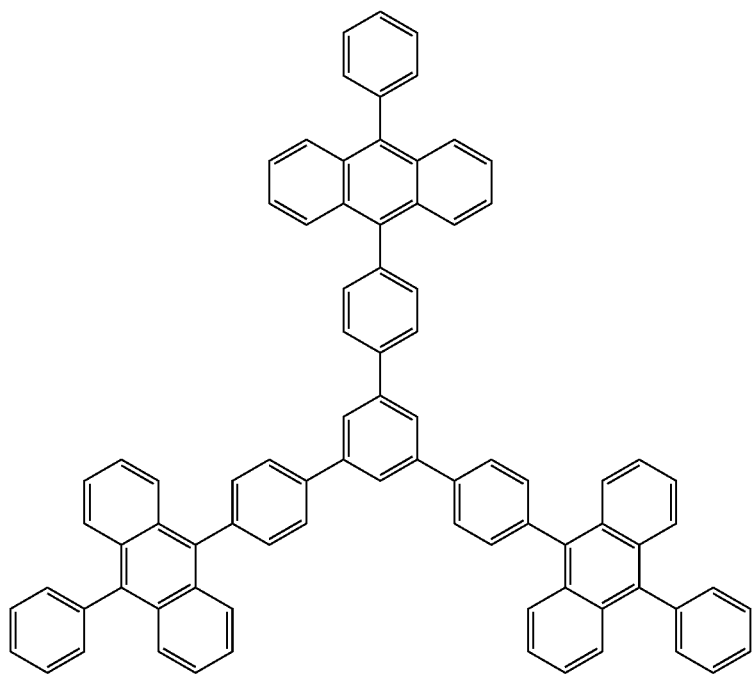
EM51
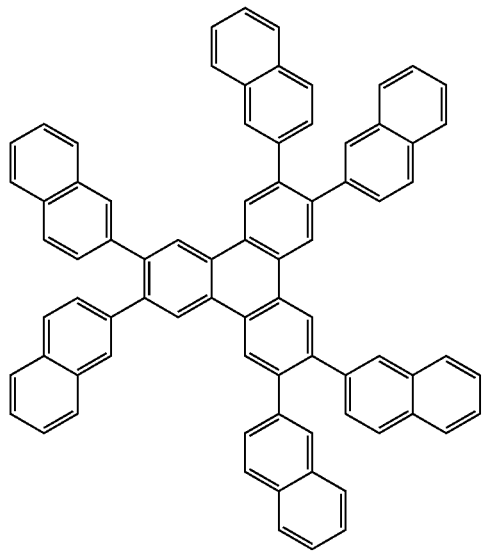
EM52
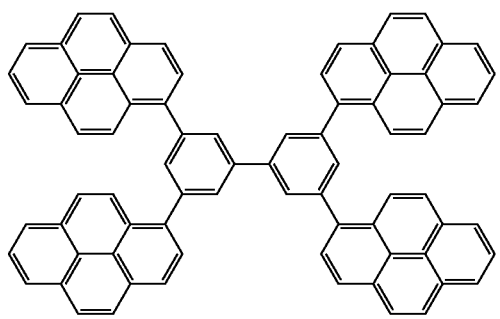
EM53

EM54
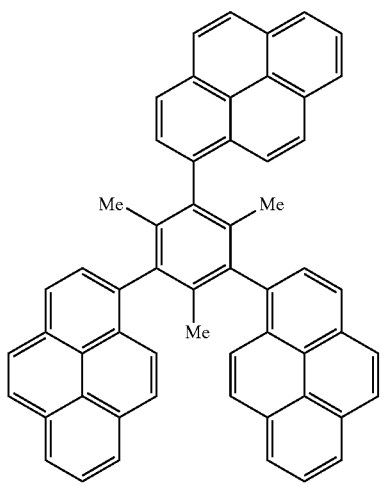
EM55
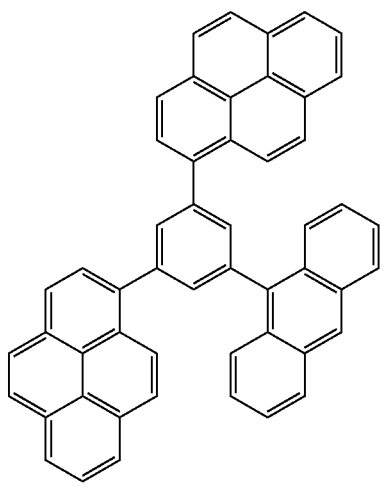
EM56
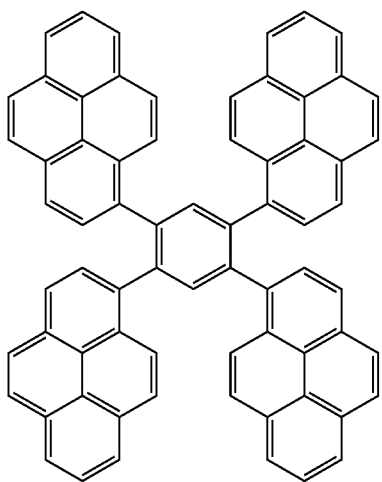
Specific examples of the arylamine compounds represented by the above general formulae (V), (V-a) and (V-b) are shown in the following.
EM57
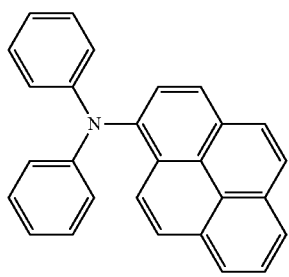
EM58
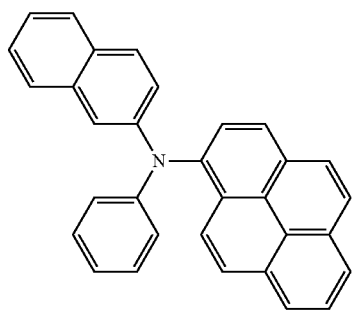

-continued
EM59
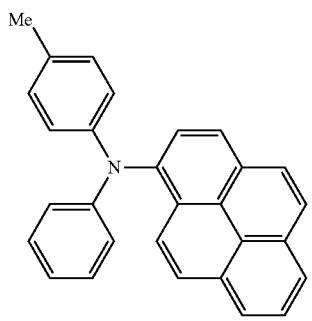
EM60
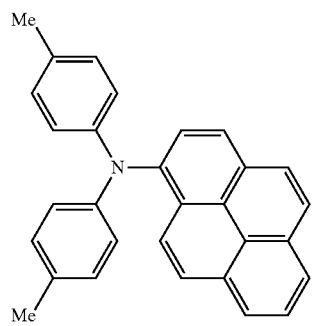
EM61
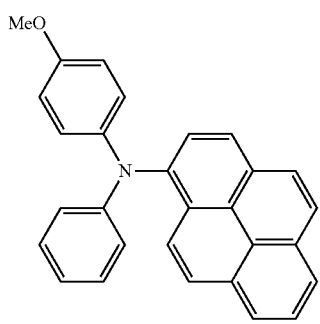
EM62
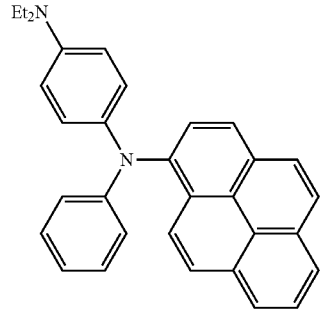
EM63
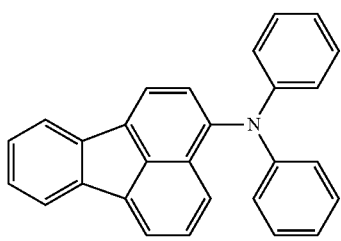
EM64
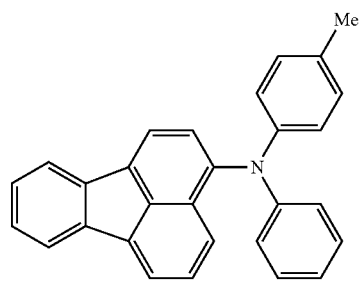
EM65
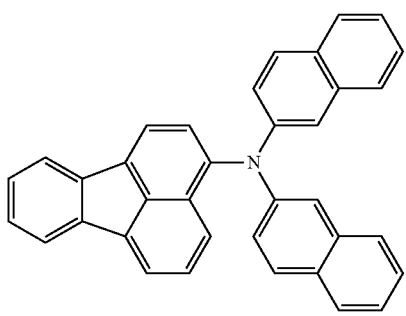
EM66
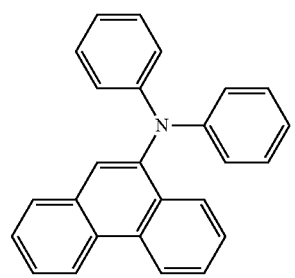
EM67
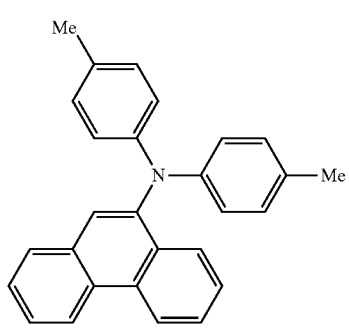
EM68
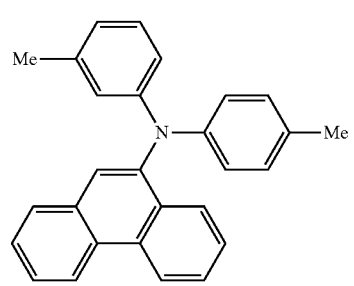

-continued
EM69
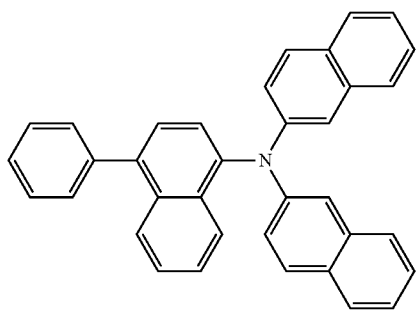
EM70
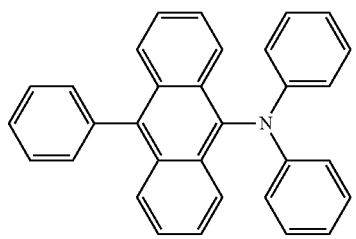
EM71
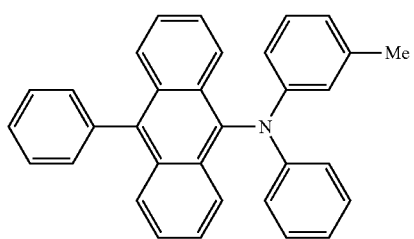
EM72
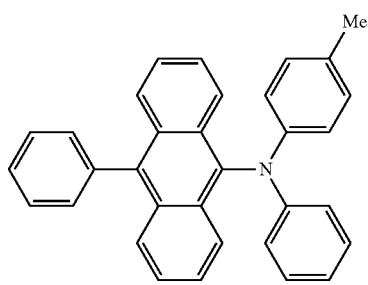
EM73
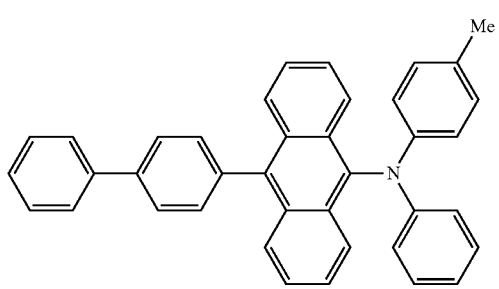
EM74
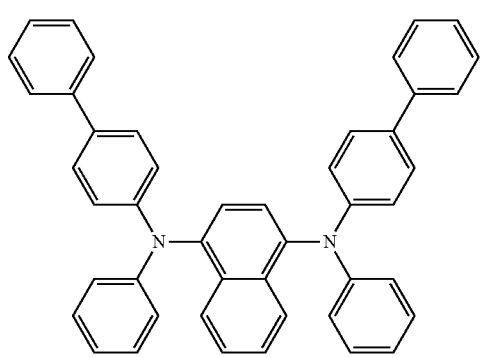
EM75
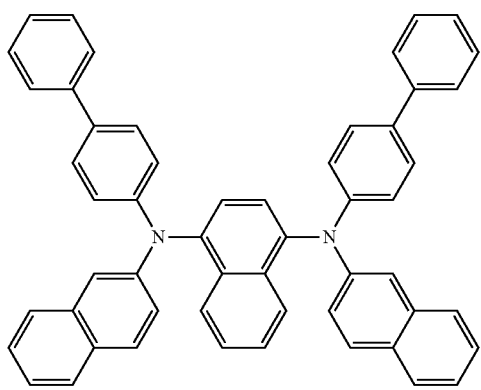
EM76
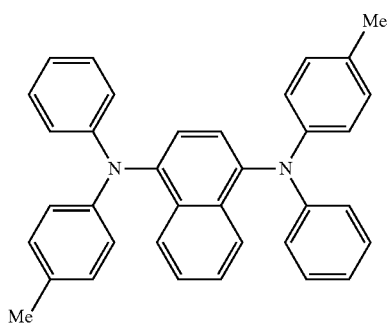
EM77
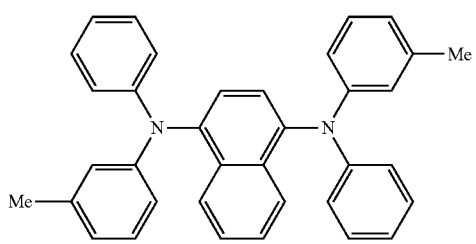
EM78
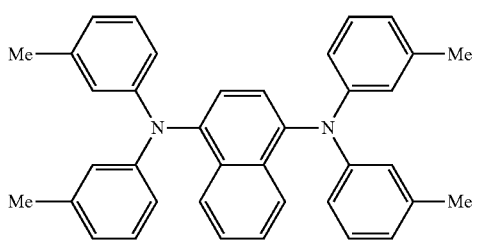

-continued
EM79 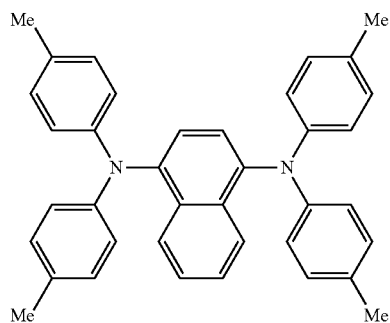 EM80 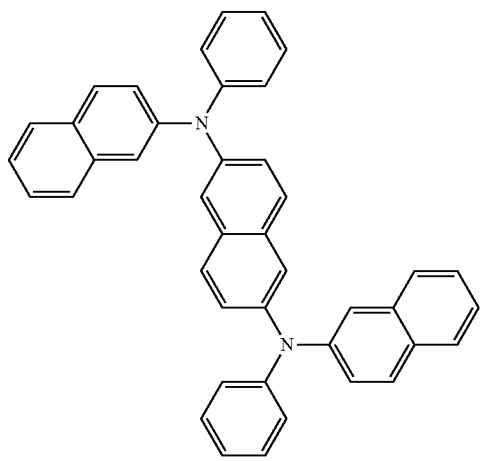
EM81 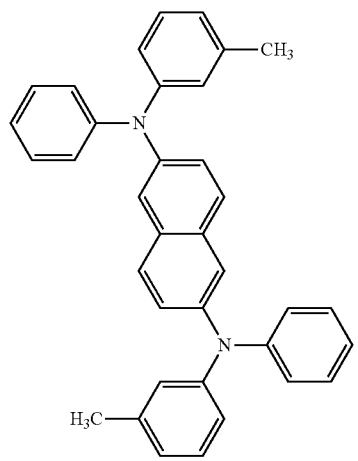 EM82 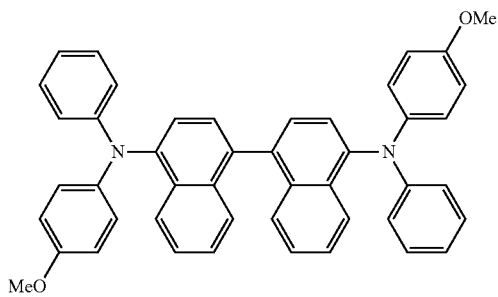
EM83 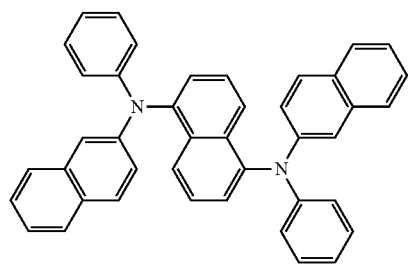 EM84 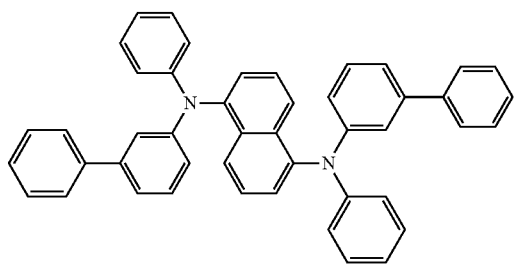
EM85 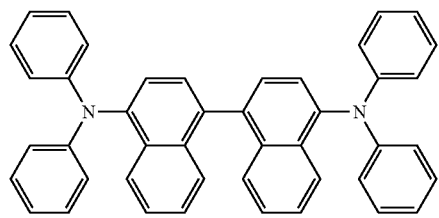 EM86 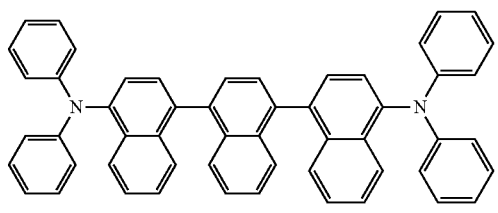

-continued
EM87
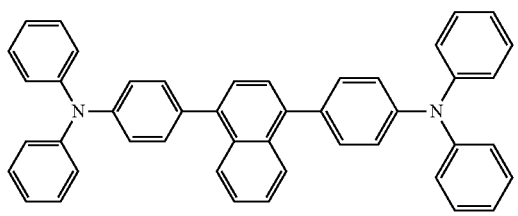
EM88
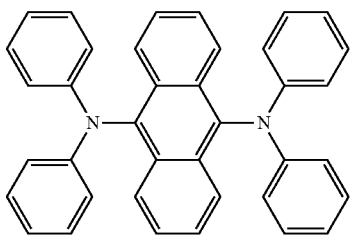
EM89
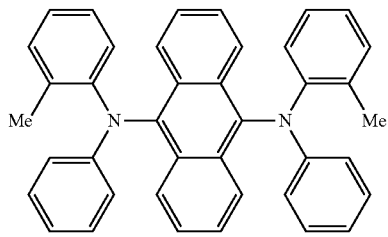
EM90
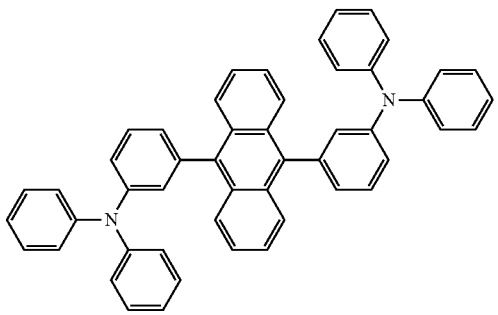
EM91
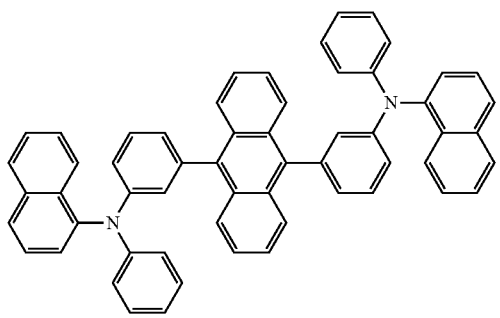
EM92
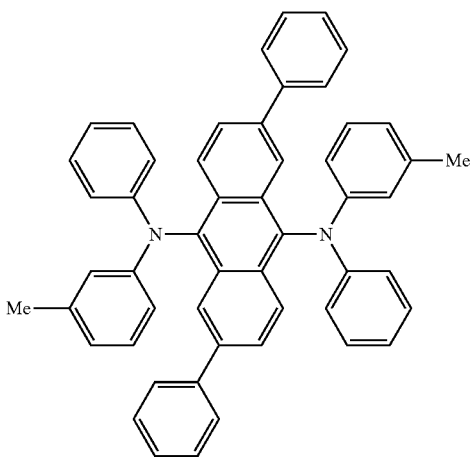
EM93
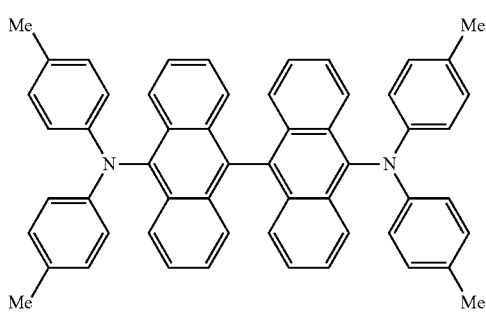
EM94
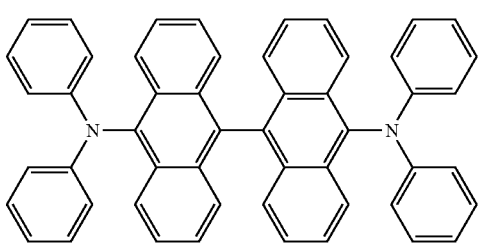
EM95
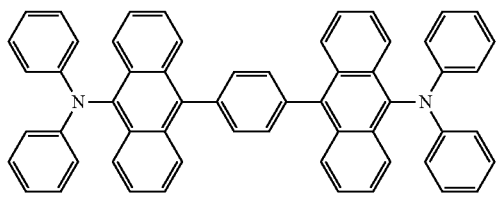
EM96
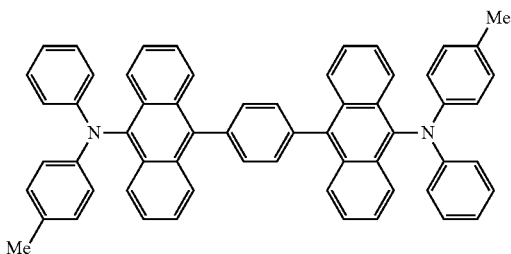

-continued
EM97
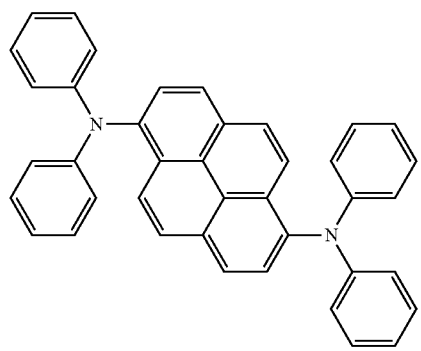
EM98
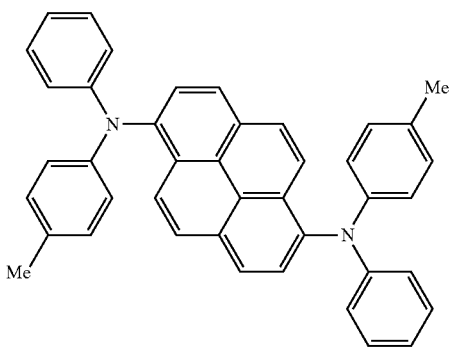
EM99
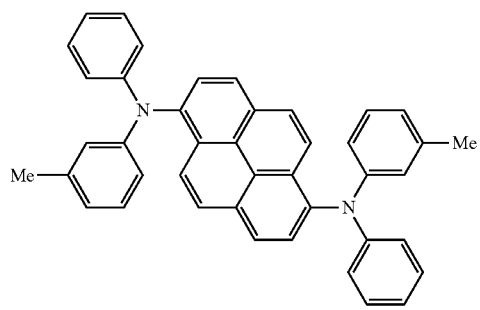
EM100
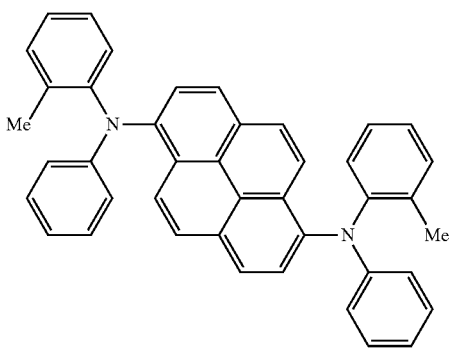
EM101
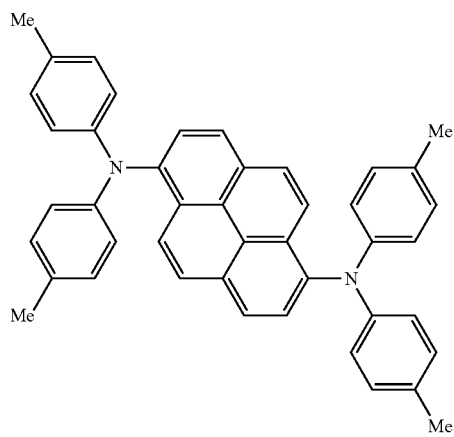
EM102
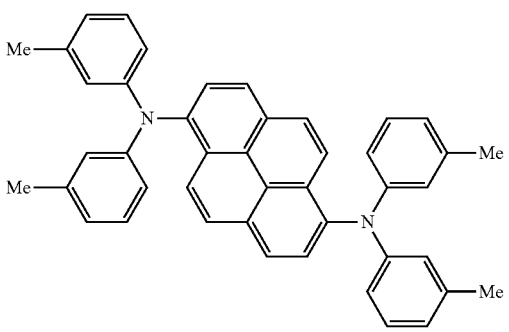
EM103
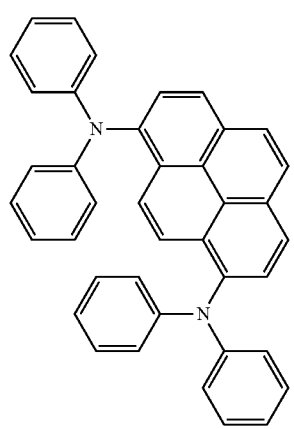
EM104
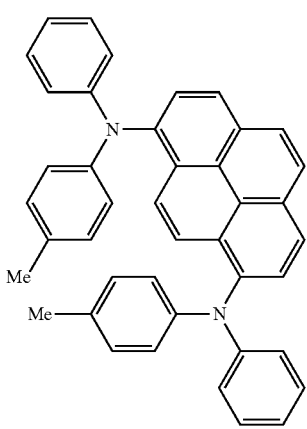

-continued
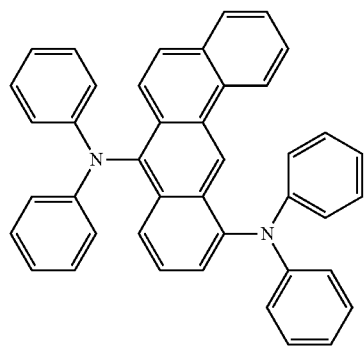
EM105
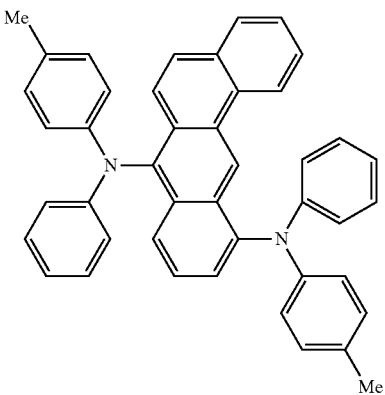
EM106
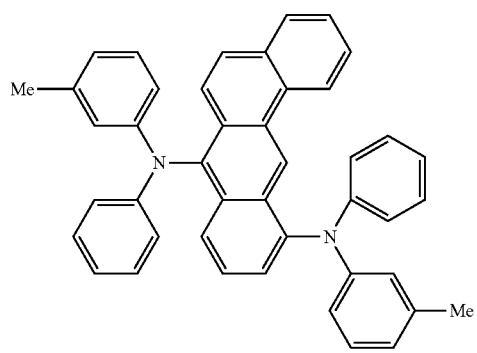
EM107
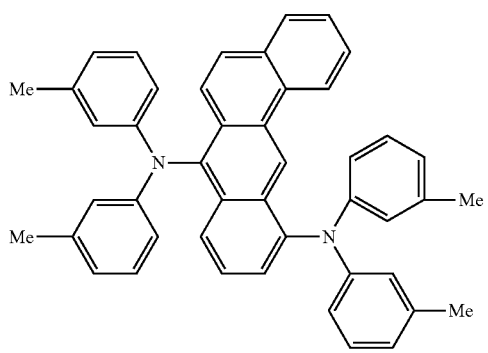
EM108
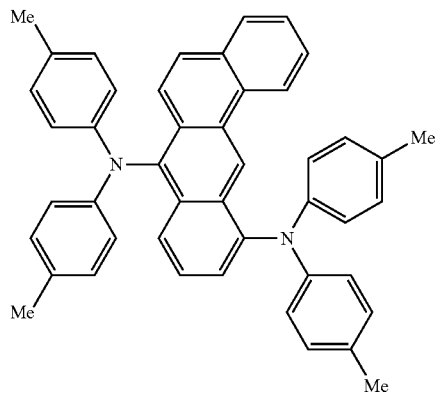
EM109
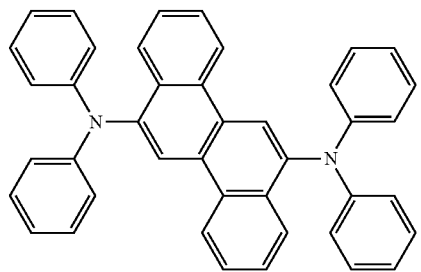
EM110
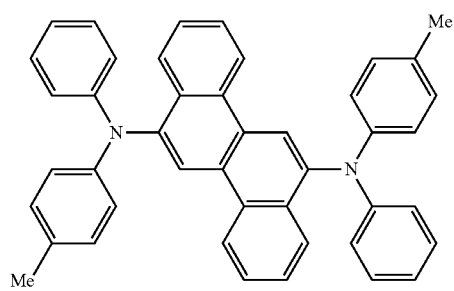
EM111
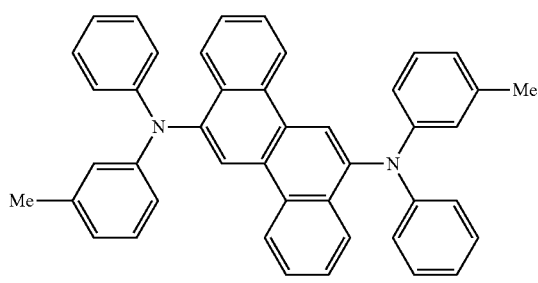
EM112

-continued
EM113
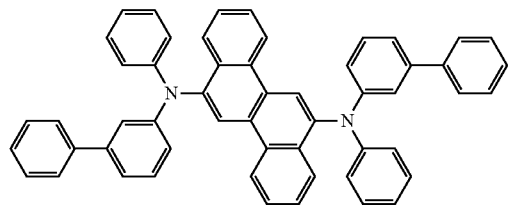
EM114
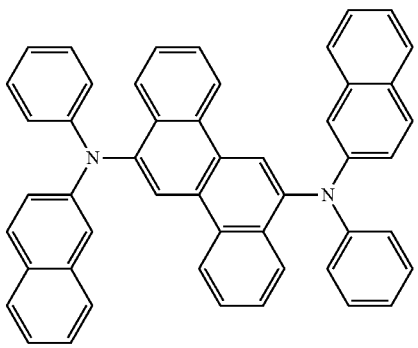
EM115
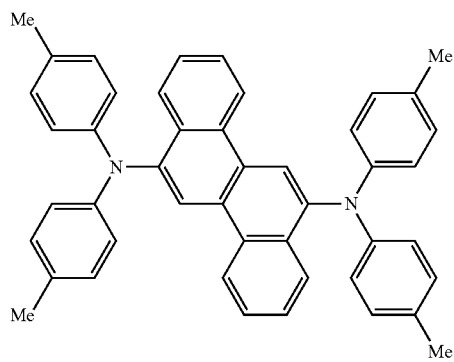
EM116
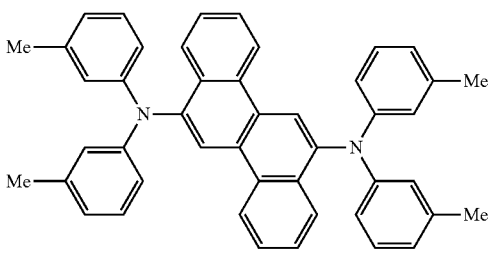
EM117
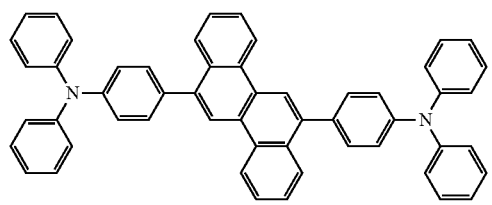
EM118
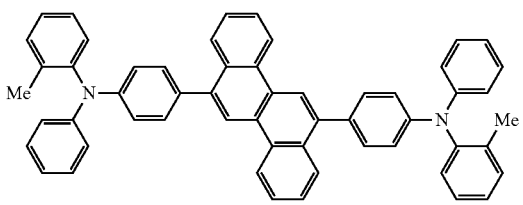
EM119
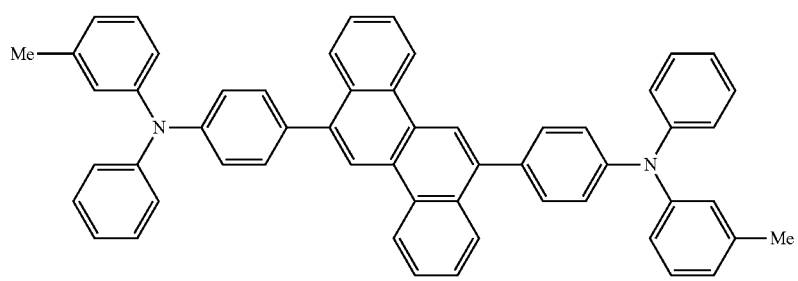
EM120
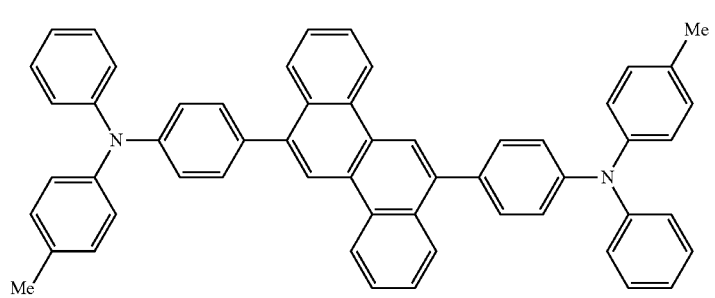

-continued
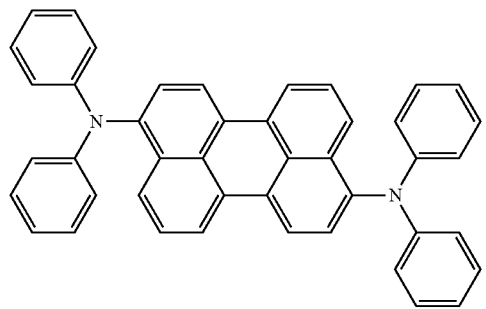
EM121
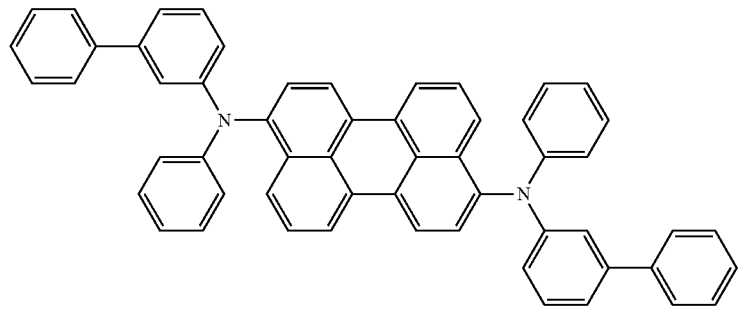
EM122
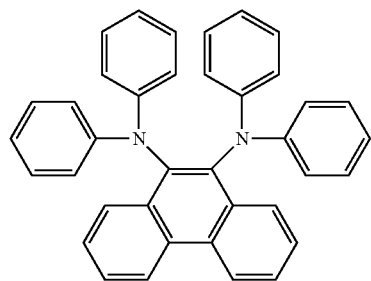
EM123
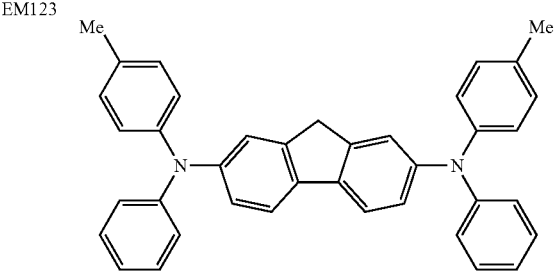
EM124
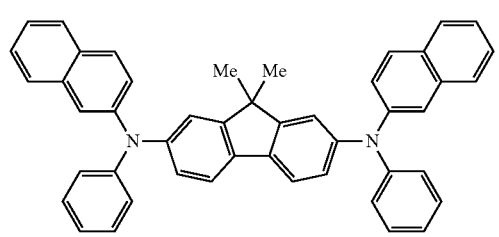
EM125
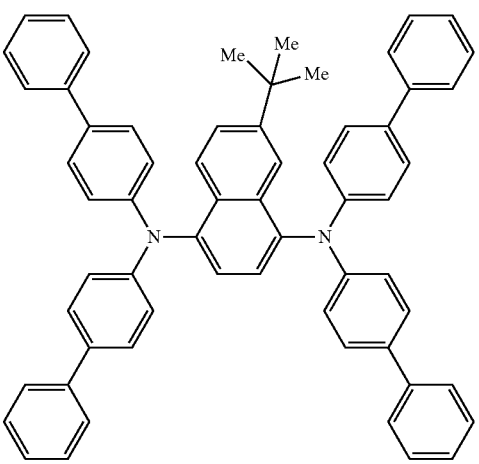
EM126

-continued
EM127
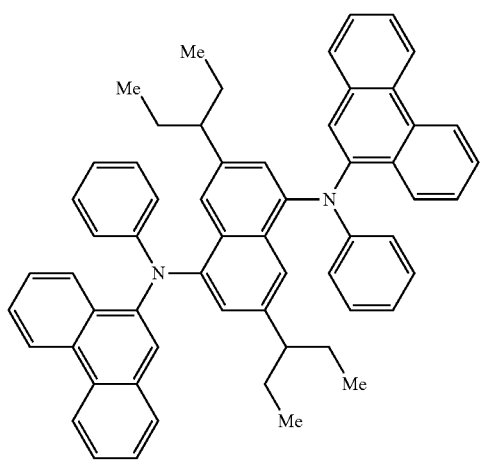
EM128
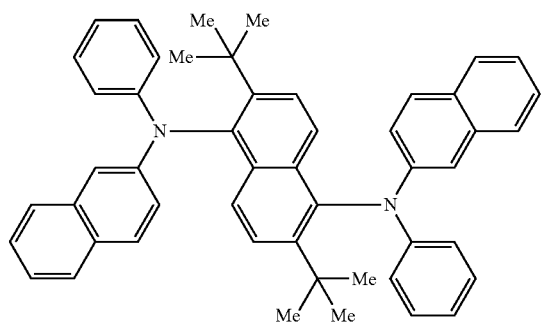
EM129
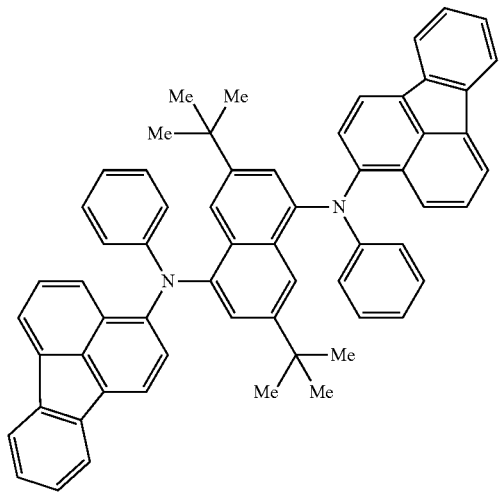
EM130
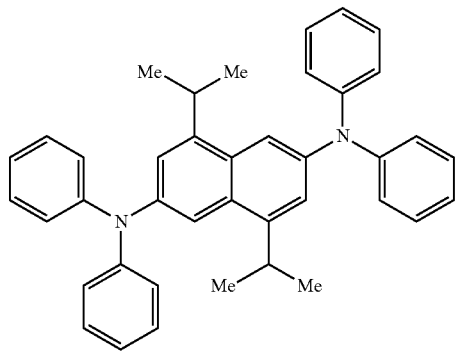
EM131
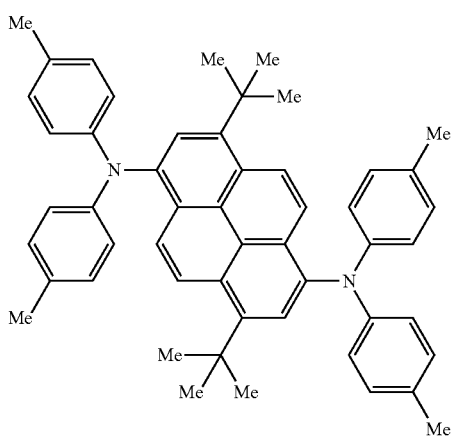
EM132
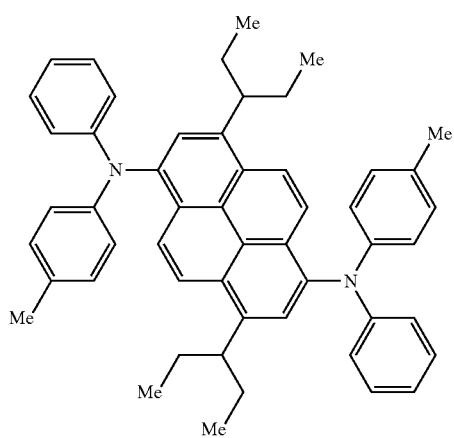

-continued
EM133
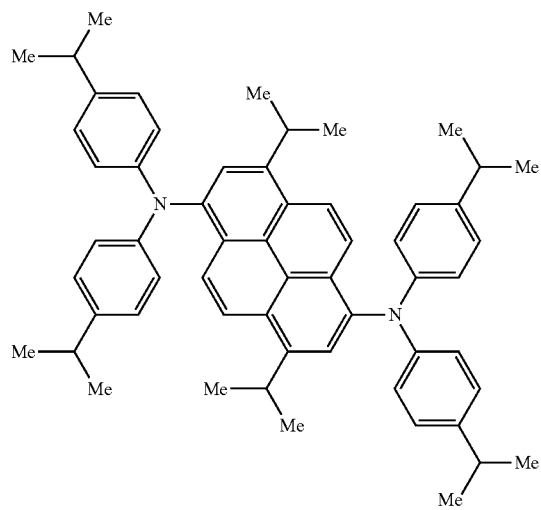
EM134
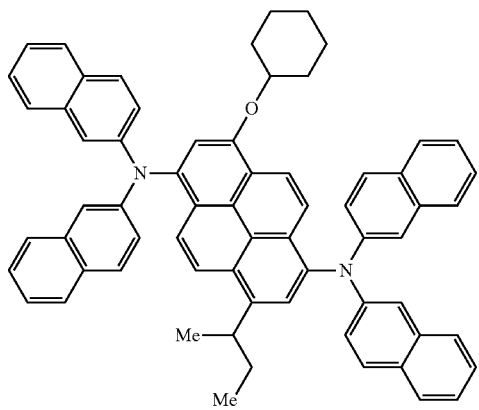
EM135
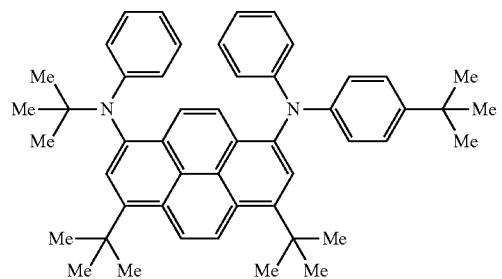
EM136
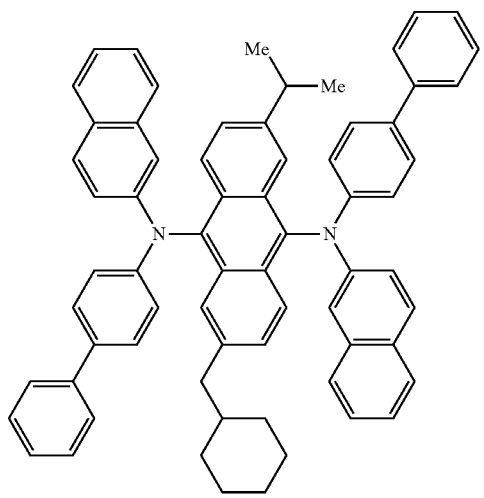
EM137
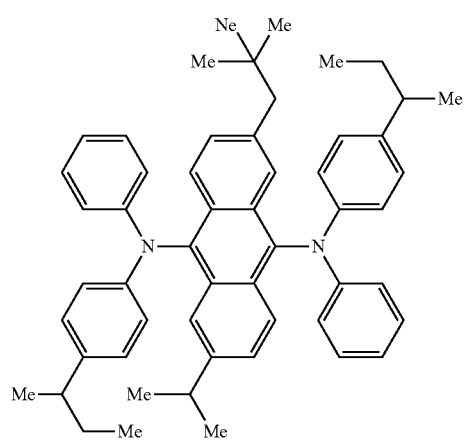
EM138
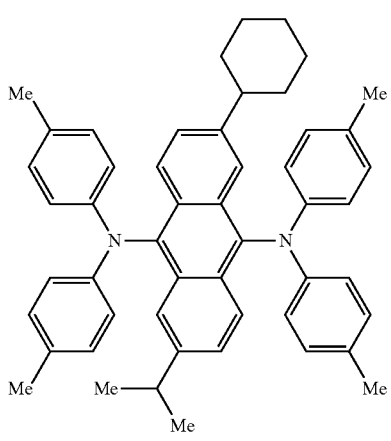

-continued
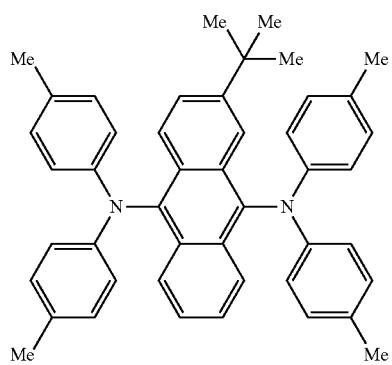
EM139
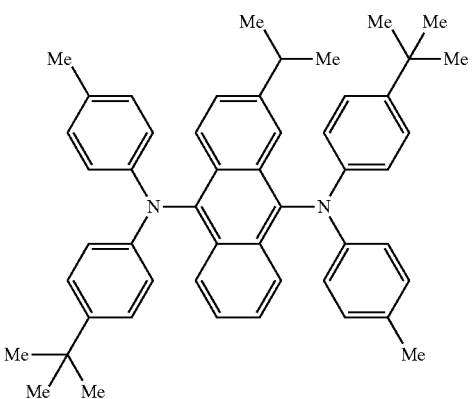
EM140
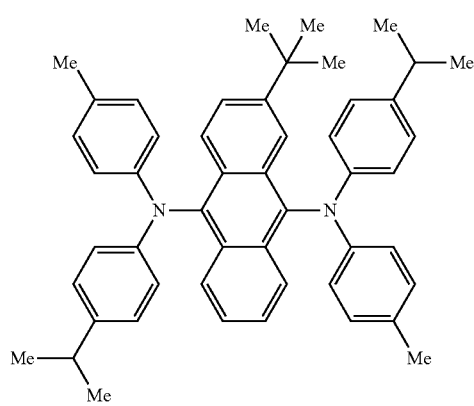
EM141
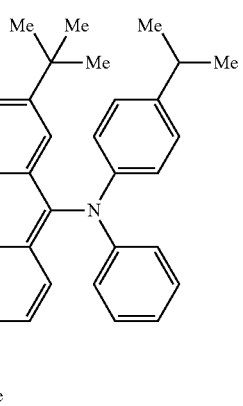
EM142
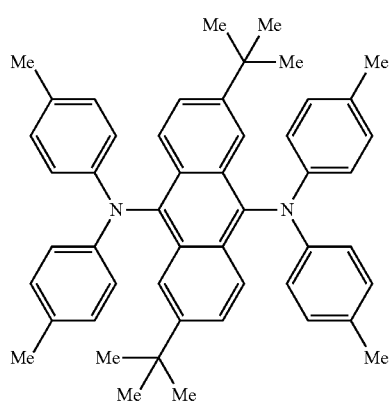
EM143
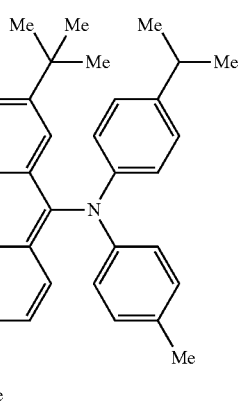
EM144
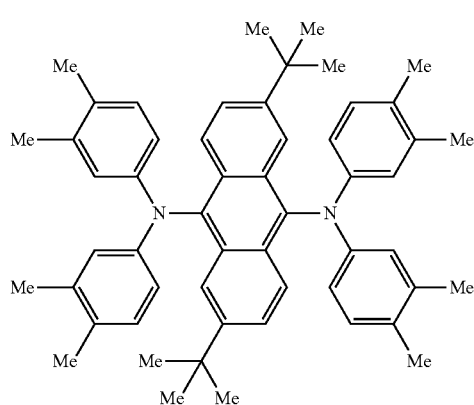
EM145
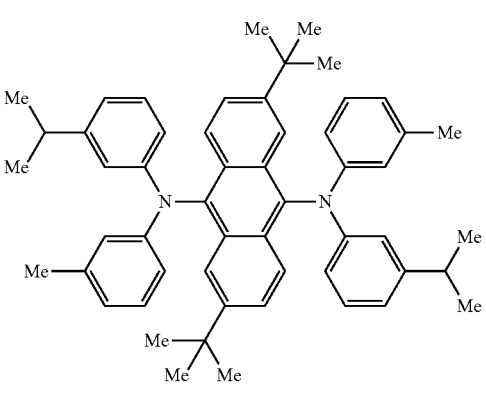
EM146

-continued
EM147
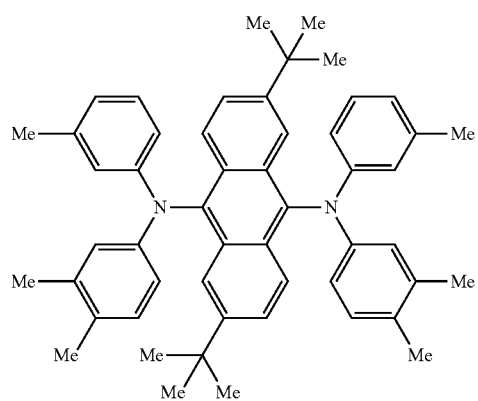
EM148
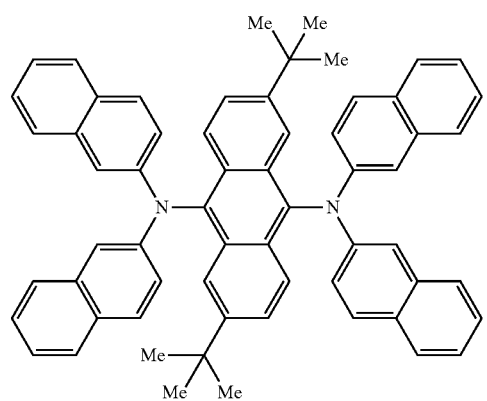
EM149
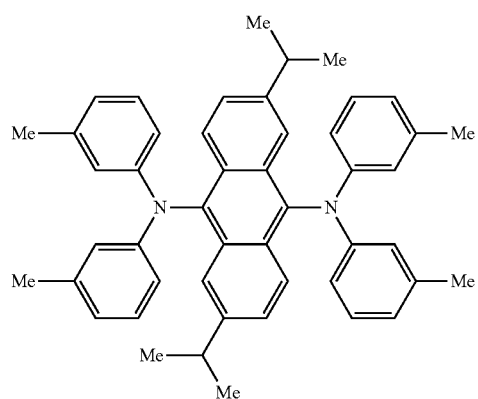
EM150
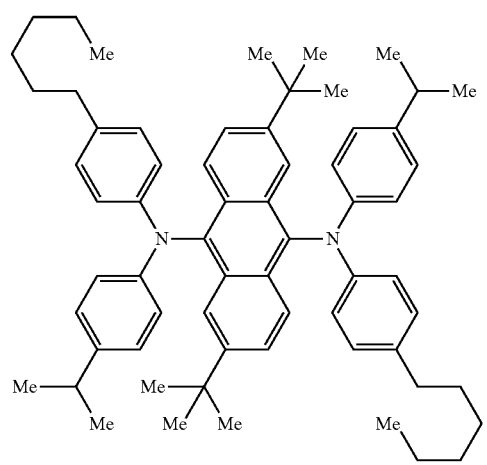
EM151
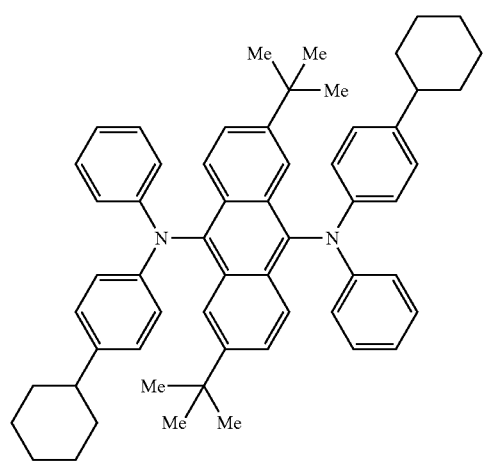
EM152
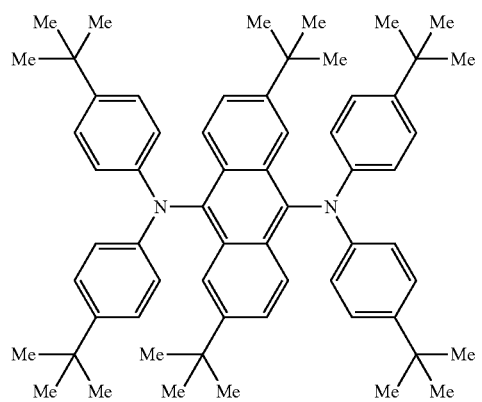

-continued
EM153
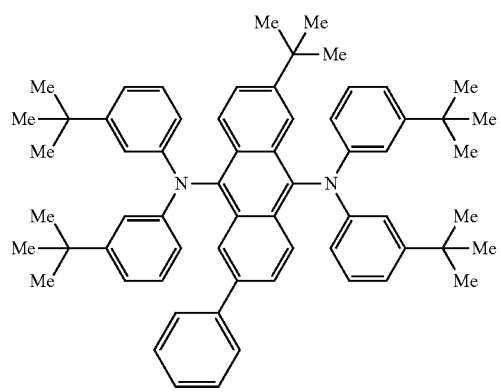
EM154
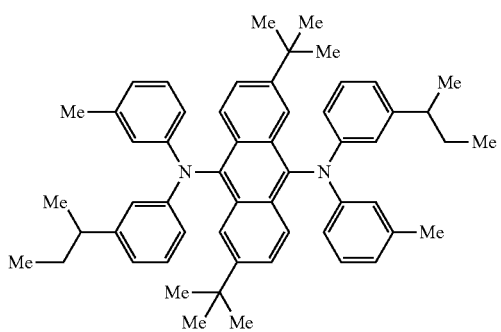
EM155
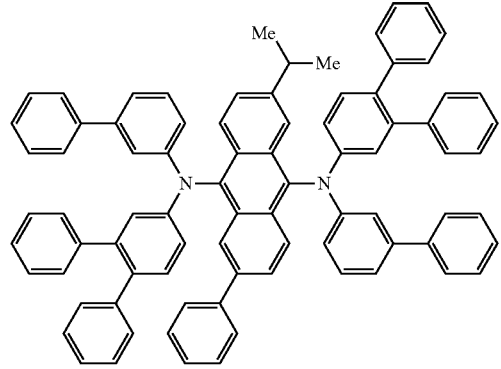
EM156
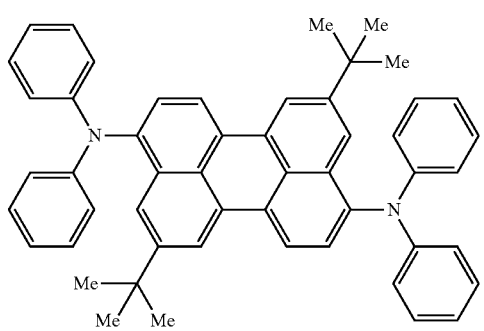
EM157
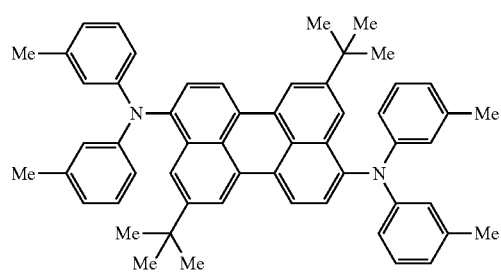
EM158
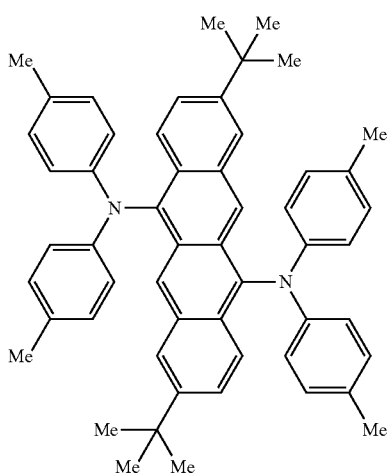
EM159
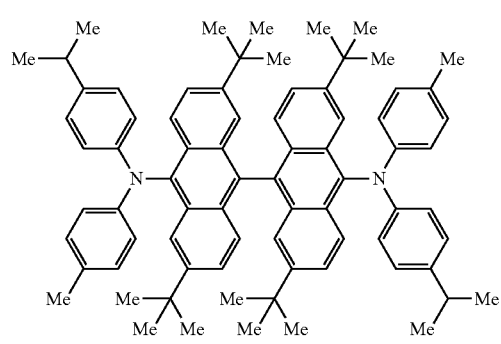
EM160
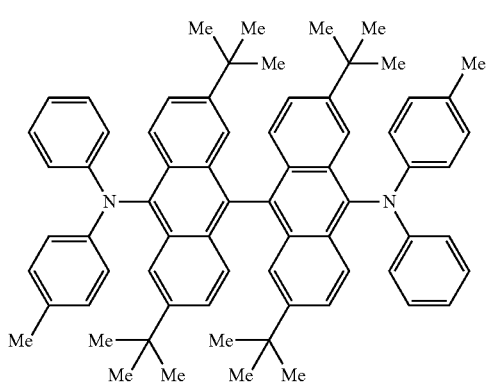

-continued
EM161
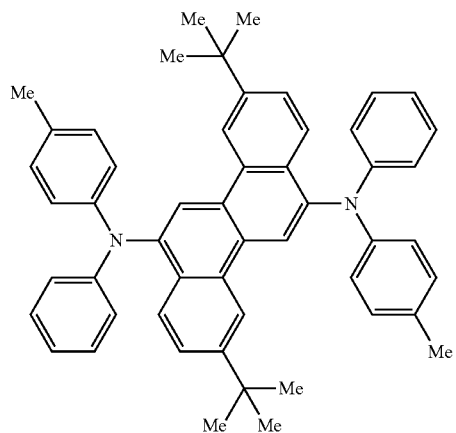
EM162
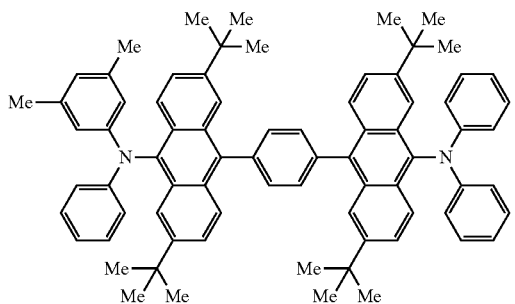
EM163
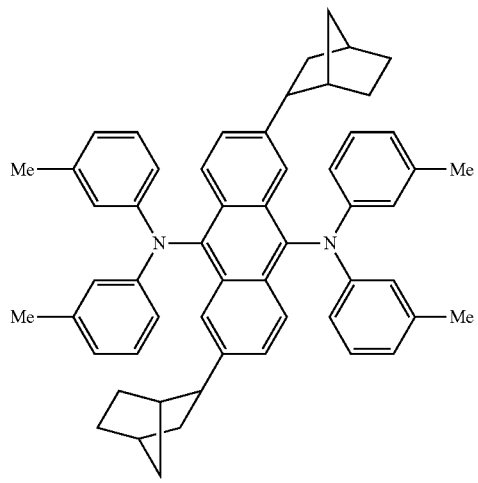
EM164
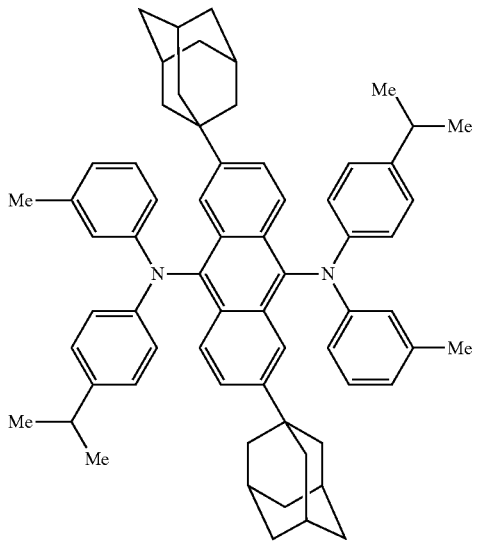
EM165
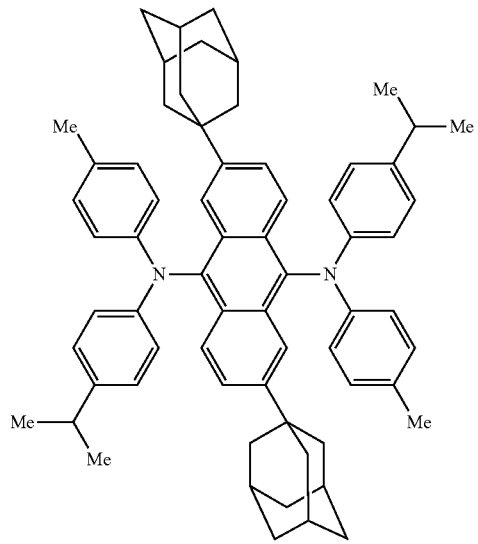
EM166
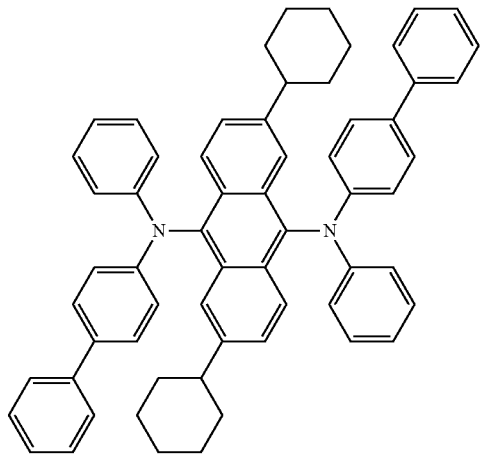

-continued
EM167
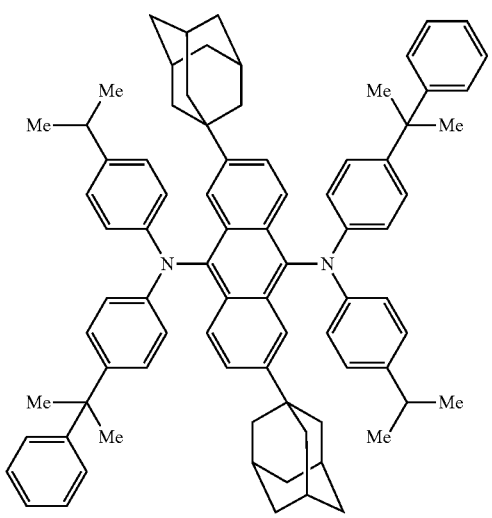
EM168
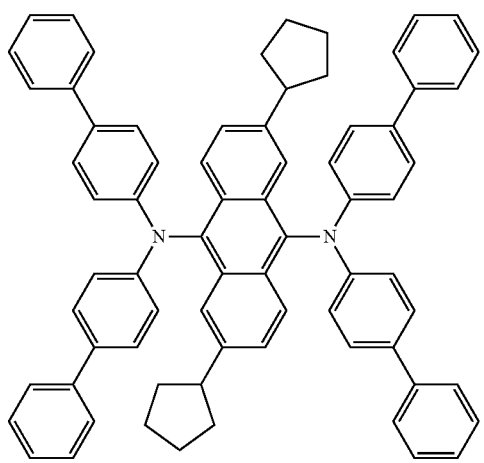
EM169
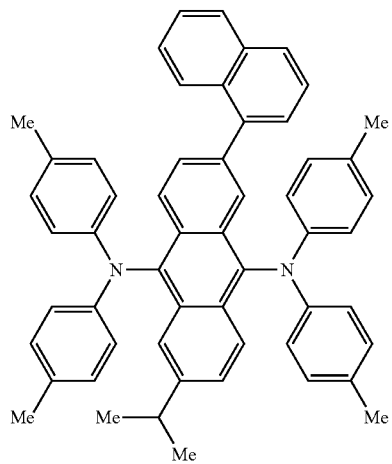
EM170
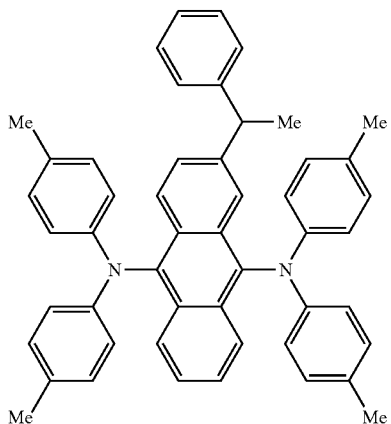
EM171
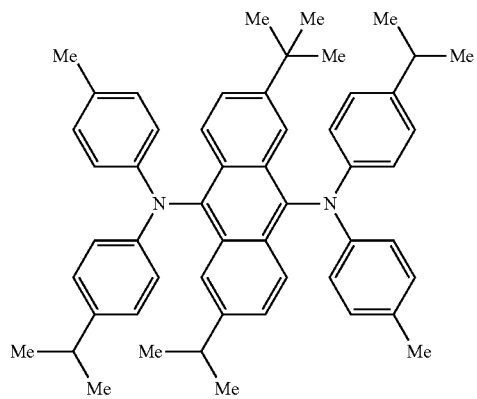
EM172
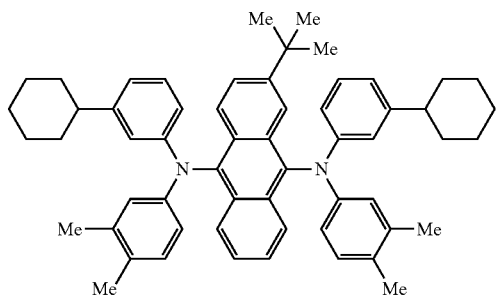

-continued
EM173
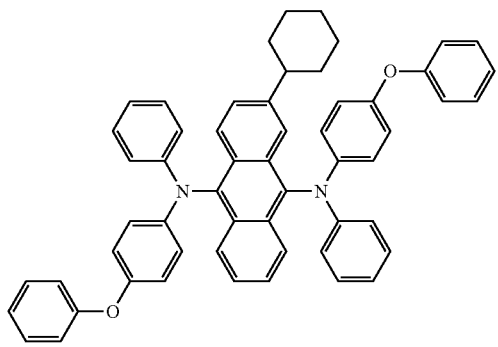
EM174
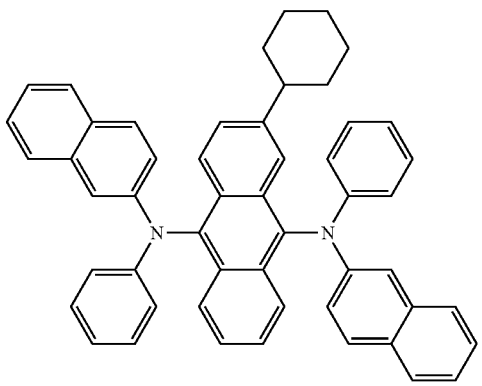
EM175
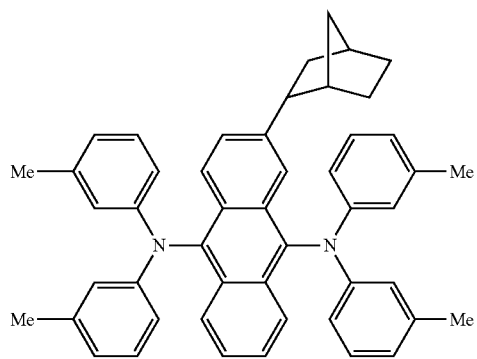
EM176
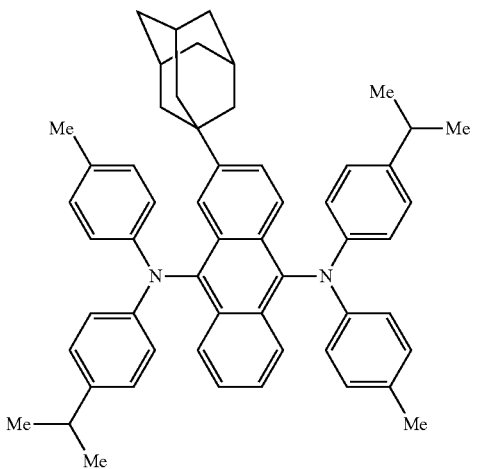
EM177
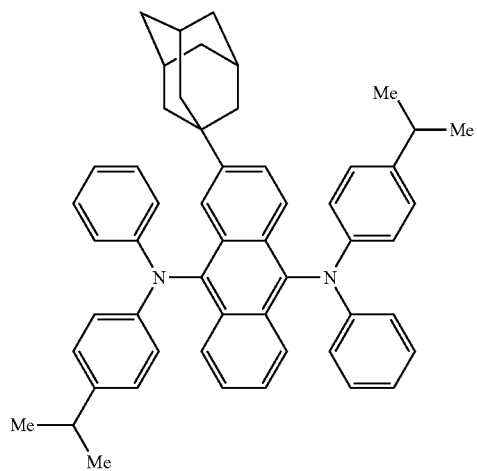
EM178
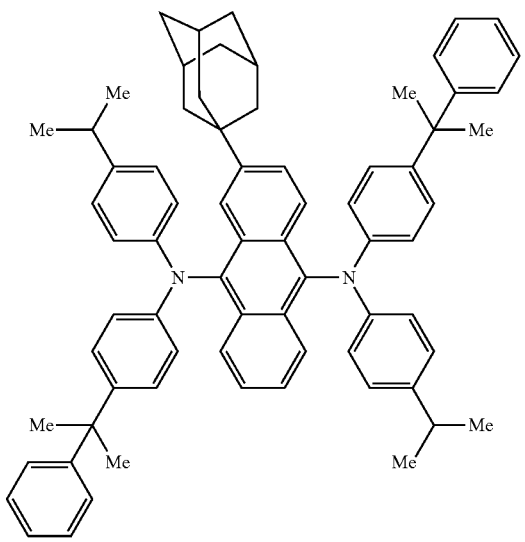

-continued
EM179
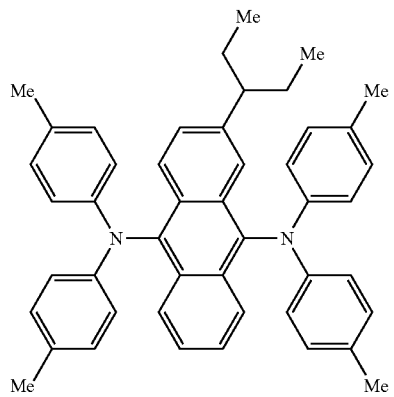
EM180
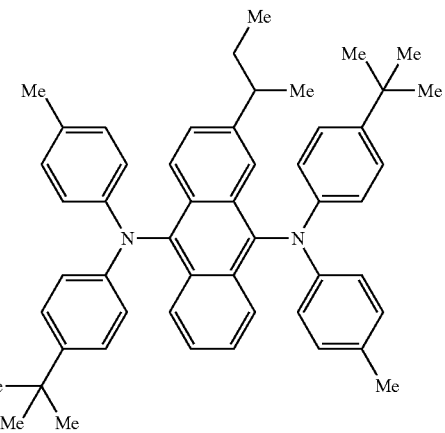
EM181
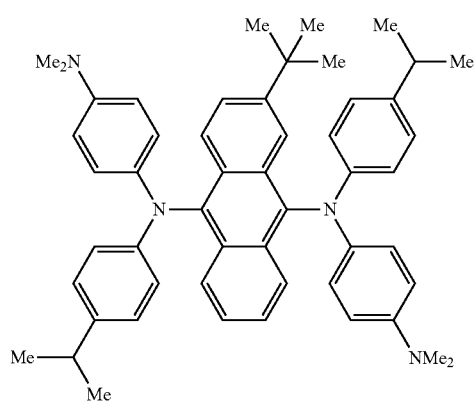
EM182
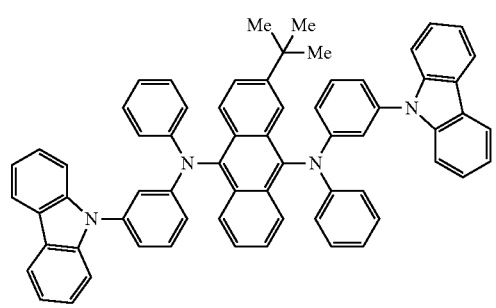
EM183
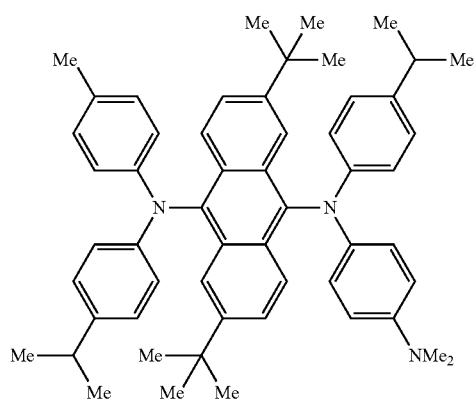
EM184
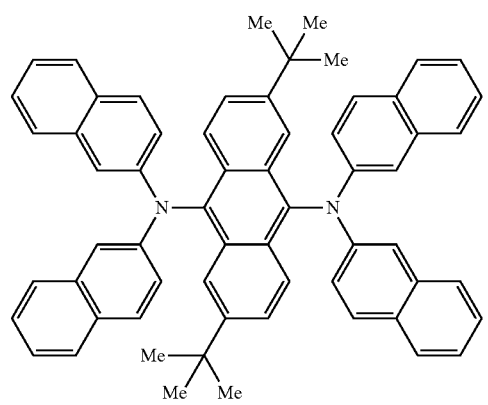
EM185
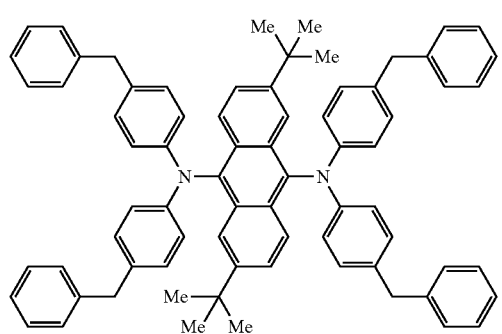
EM186
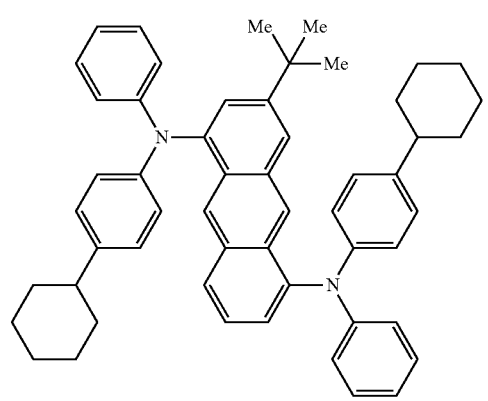

-continued
EM187
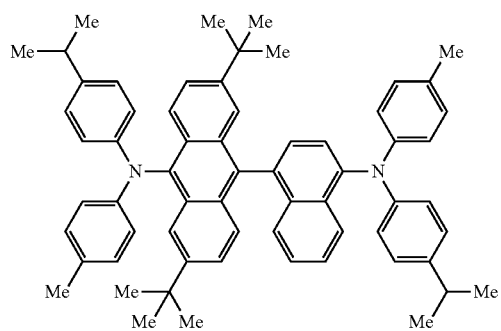
EM188
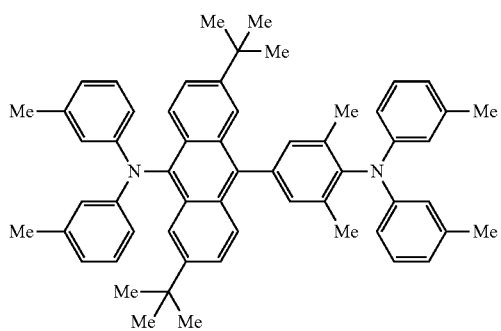
EM189
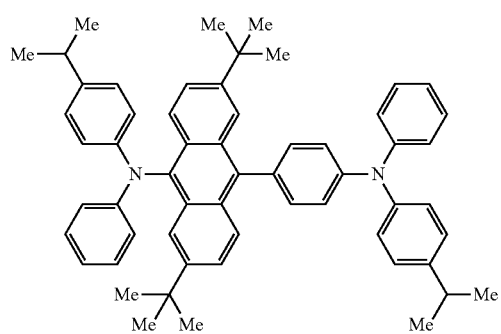
EM190
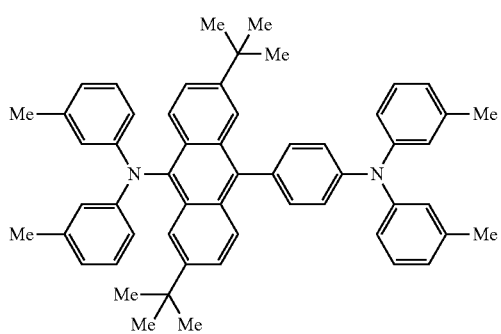
EM191
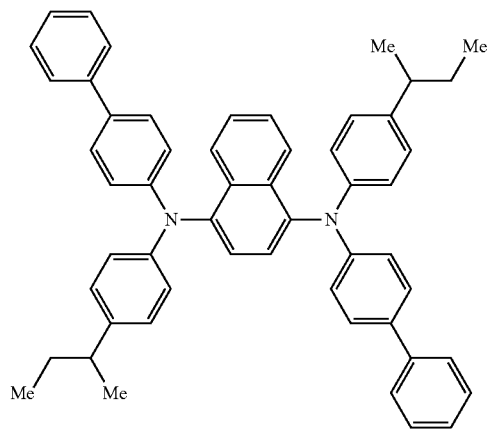
EM192
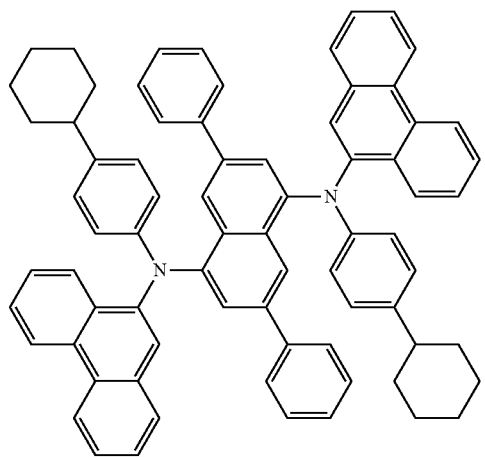
EM193
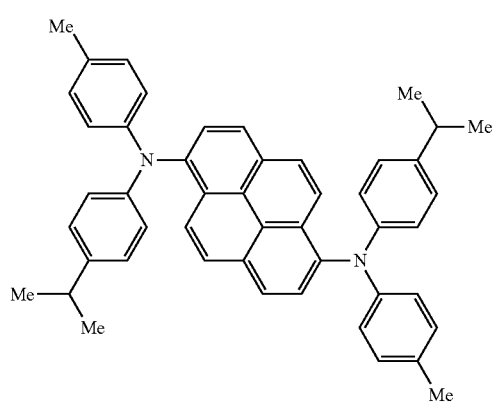
EM194
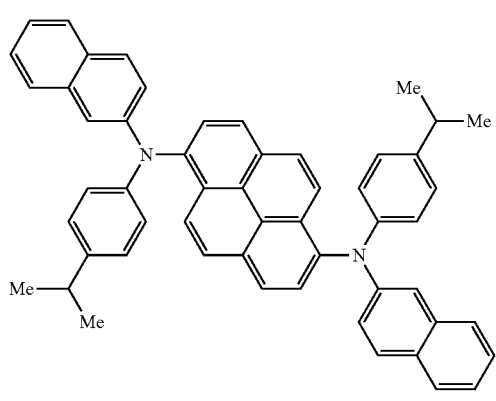

-continued
EM195
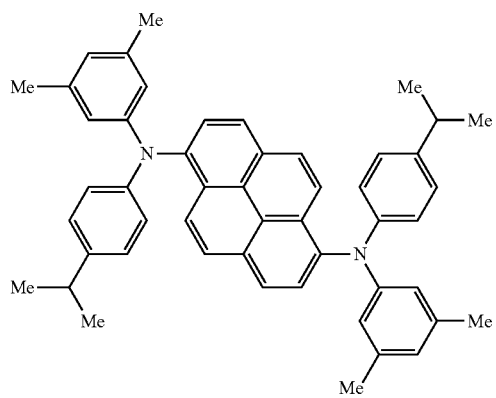
EM196
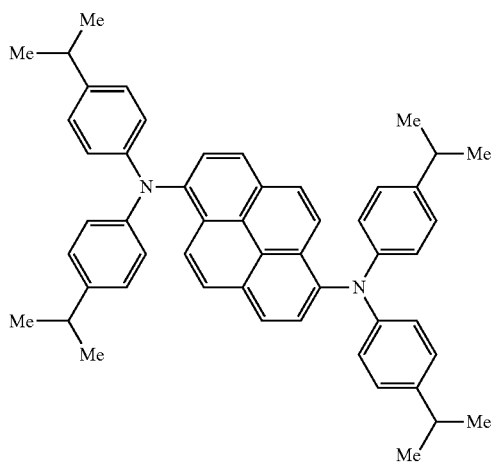
EM197
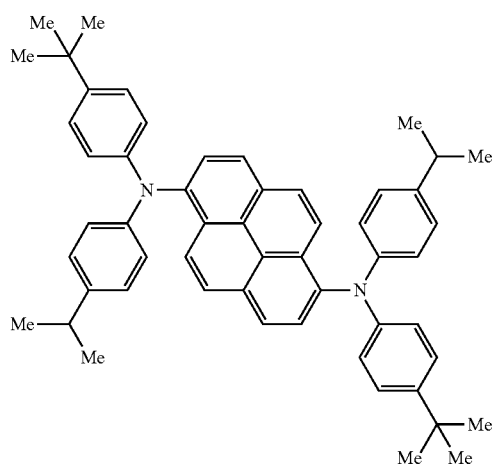
EM198
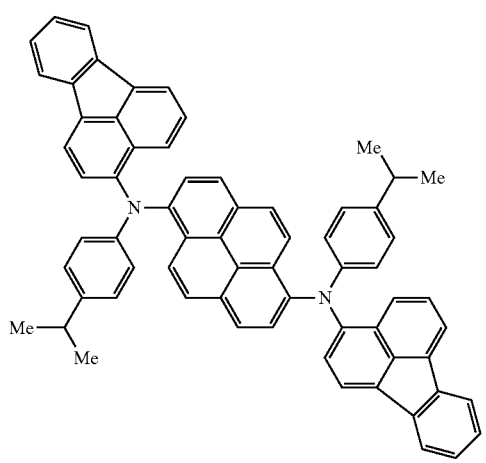
EM199
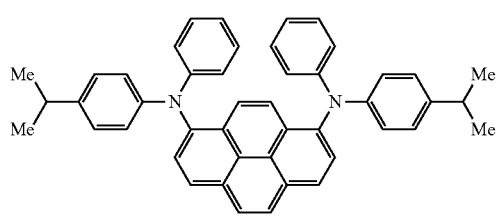
EM200
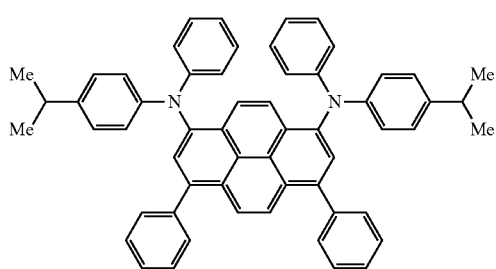
EM201
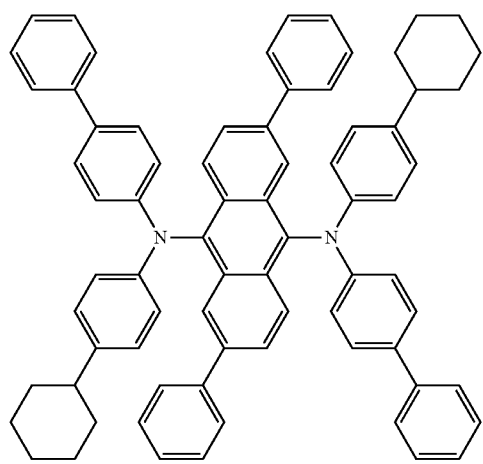
EM202
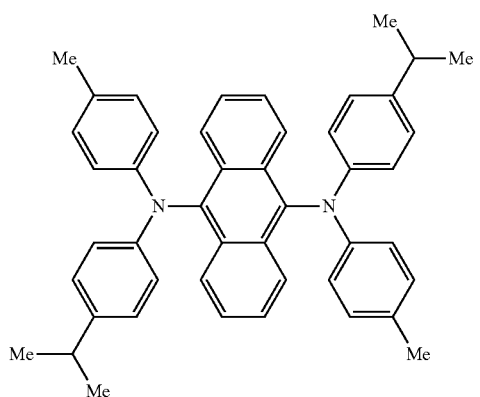

-continued
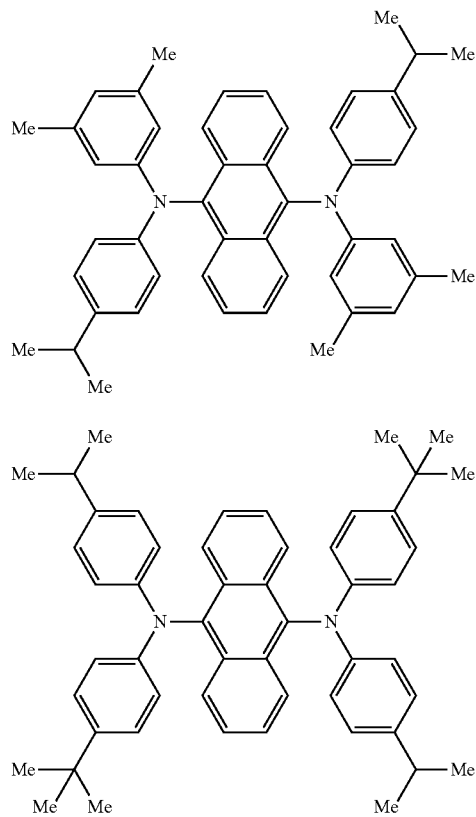
EM203
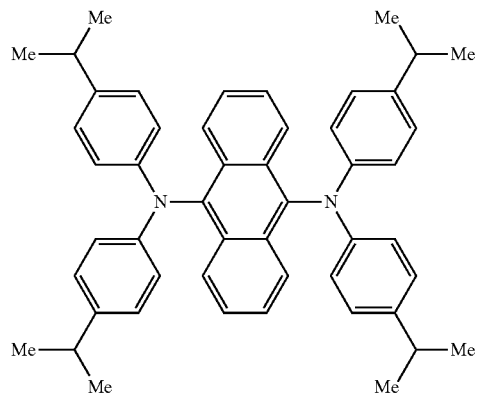
EM204
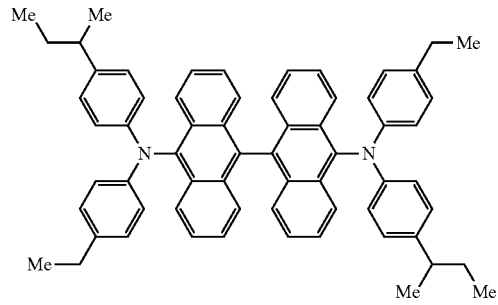
EM205
EM206
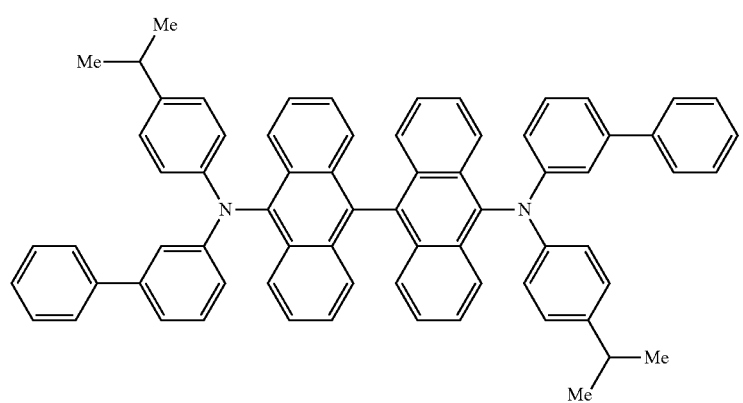
EM207
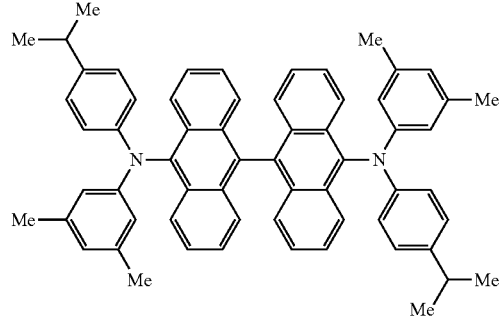
EM208
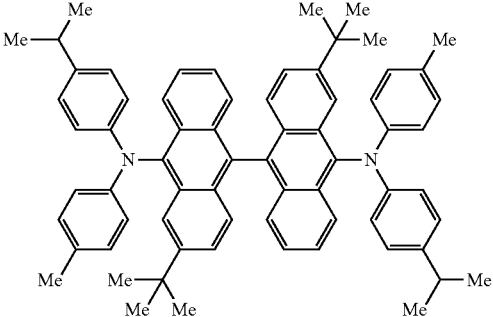
EM209

-continued
EM210
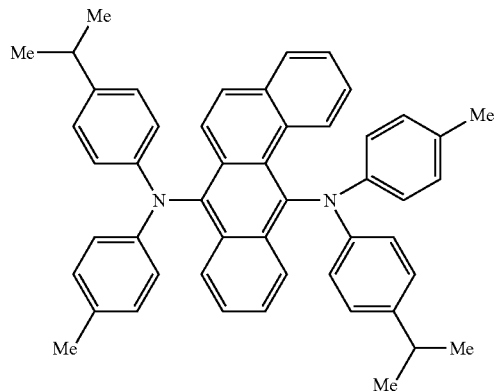
EM211
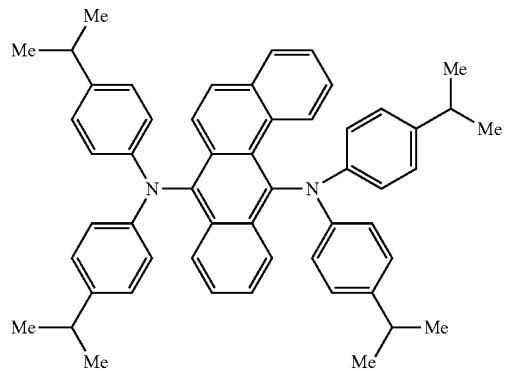
EM212
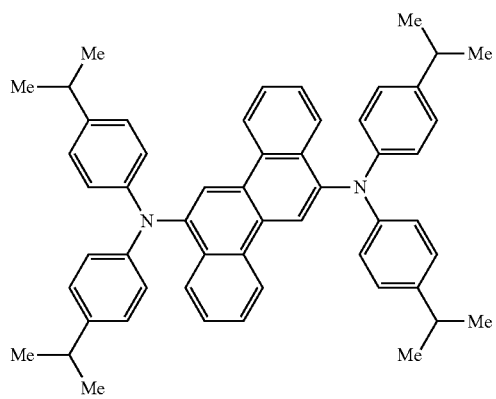
EM213
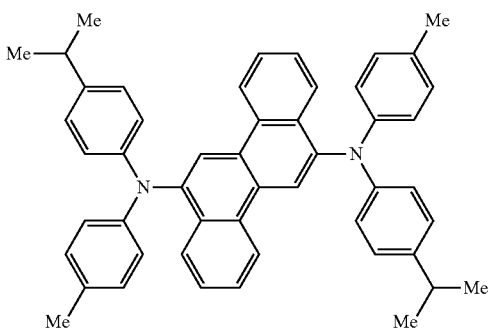
EM214
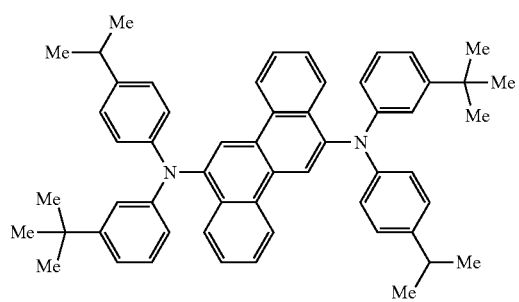
EM215
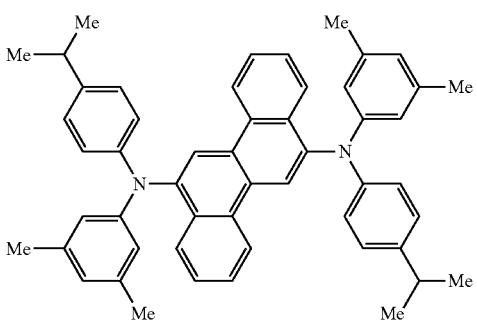
EM216
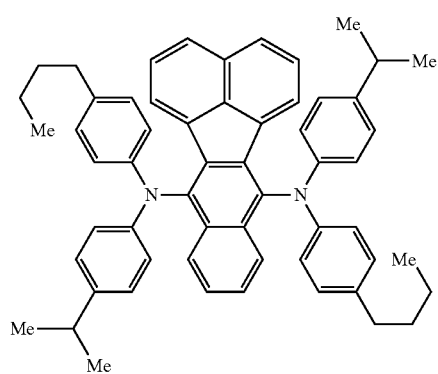
EM217
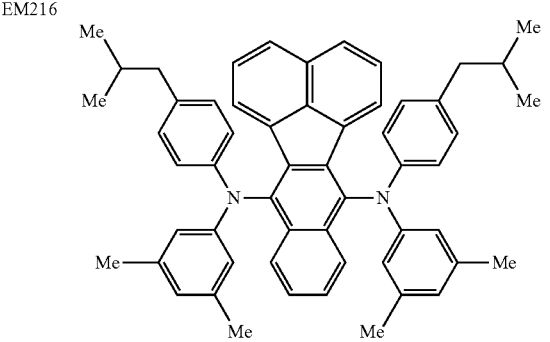

-continued
EM218
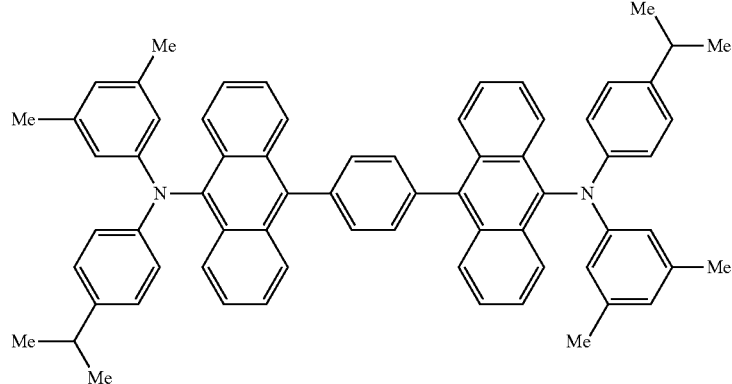
EM219
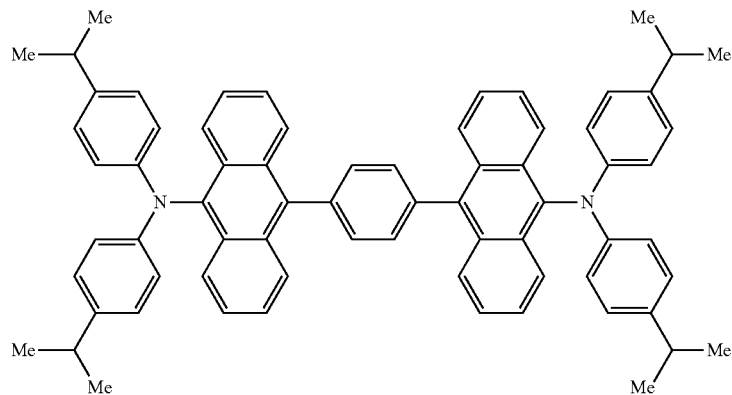
EM220  EM221
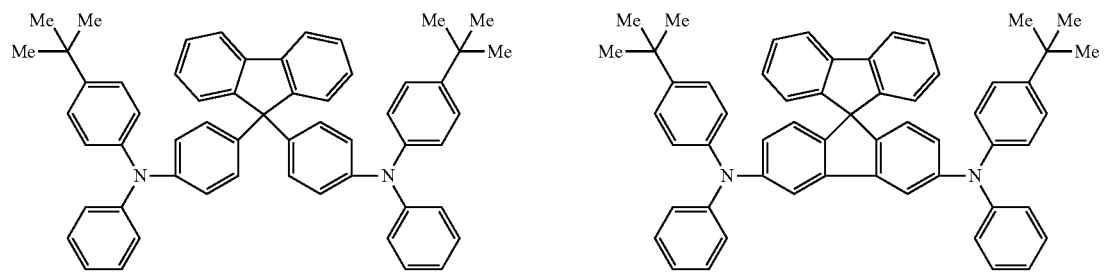
EM222
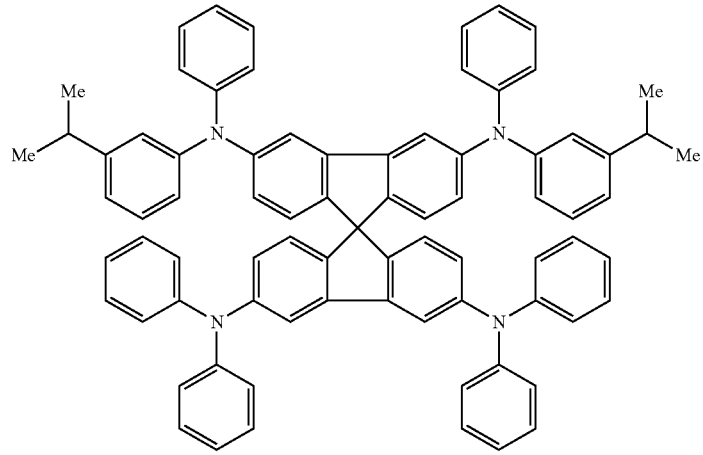

-continued
EM223
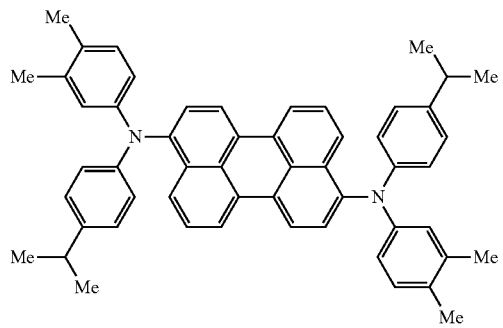
EM224
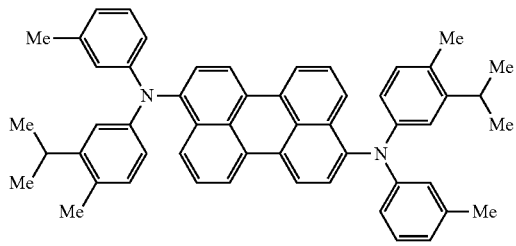
EM225
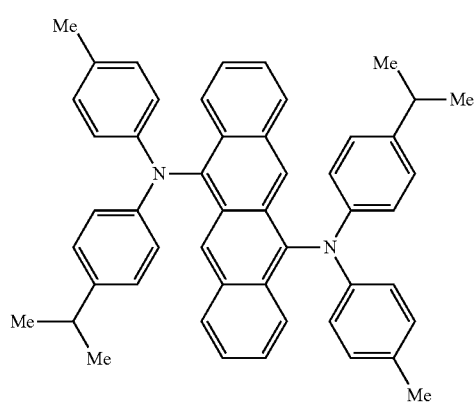
EM226
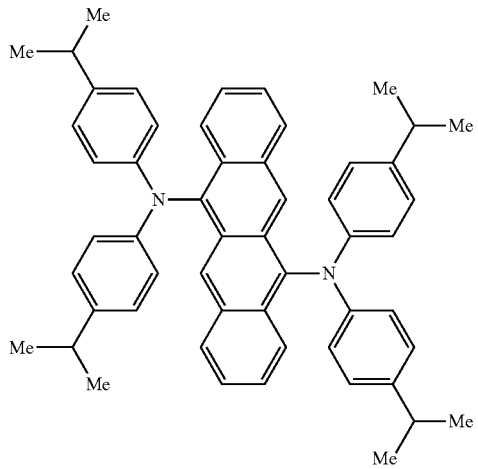
EM227
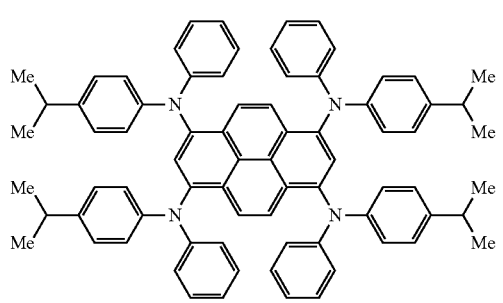
EM228
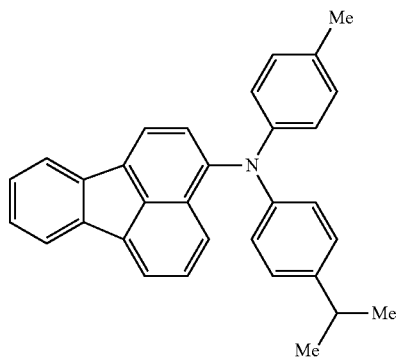
EM229
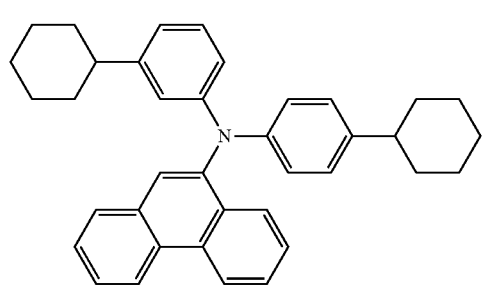
EM230
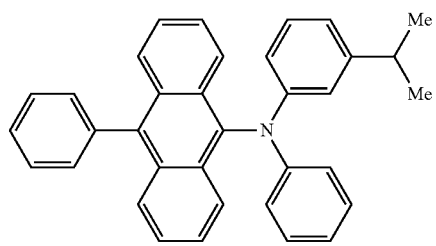

-continued

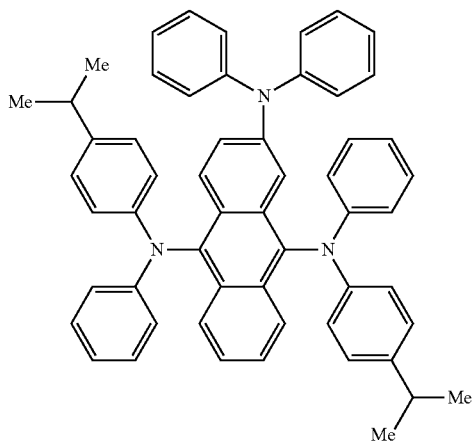

EM231

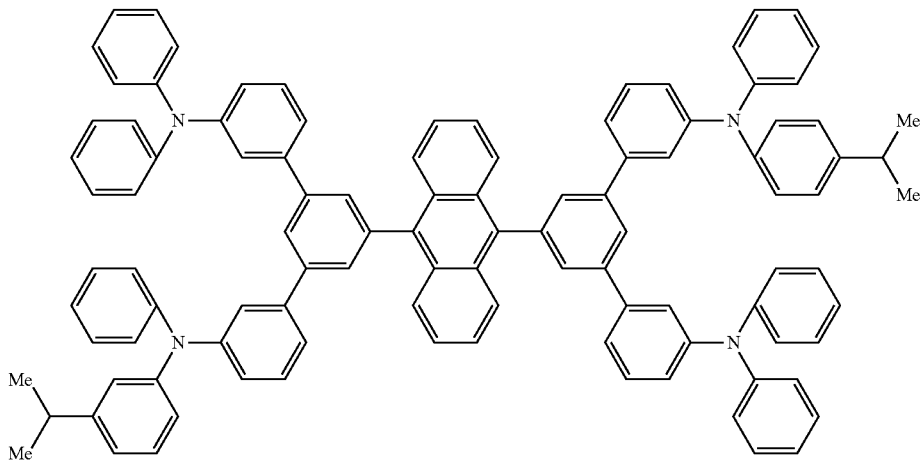

EM232

In the present invention, the ratio of the amount by weight of the arylamine of component (A) to the amount by weight of the anthracene derivative of component (B) in the layer of an organic light emitting medium is in the range of 1:99 to 99:1. It is preferable that the ratio of the amounts is suitably selected in accordance with the type of the compounds used. It is more preferable that, taking it into consideration that the compound of component (A) has the hole transporting property and the compound of component (B) has the electron transportation property, the ratio of the amounts is selected in a manner such that the life and the efficiency of the obtained device are maximized.

It is preferable that the ratio of the amount by weight of component (A) to the amount by weight of component (B) is in the range of 1:99 to 20:80. A particularly high efficiency can be obtained in this range.

It is preferable that the layer of an organic light emitting medium has a thickness in the range of 5 to 200 nm and more preferably in the range of 10 to 40 nm since the voltage applied to the device can be lowered to a great extent.

Due to the use of component (A) in combination with component (A) for the layer of an organic light emitting medium, the efficiency can be increased by 3 to 5 times as much as the efficiency obtained by using component (A) alone and the life can be increased by at least 3 times, and by at least 10 times when optimized, as long as the life obtained by using component (A) alone.

Due to the use of the arylamine represented by general formula (V) as component (A), the concentration quenching due to an increase in the association of molecules can be prevented since the steric hindrance increases and the life can be further increased. When a branched alkyl group is introduced into the substituent of amino group or the condensed aromatic ring, the half width of the spectrum of the emitted light which can be used as the index for the purity of color is decreased since the steric repulsion between the condensed aromatic ring and the substituent of amino group is increased and the spectrum of the emitted light becomes sharp. Therefore, the obtained device is suitable for full color displays.

Due to the use of component (A) and component (B) in combination, the stability and the heat resistance are improved since the layer of an organic light emitting layer becomes more amorphous. It is preferable that the compound of component (B) has a glass transition temperature of 110° C. or higher. It is also preferable that the compound of component (A) has a glass transition temperature of 70° C. or higher. By mixing the compounds having the above glass transition temperatures, the glass transition temperature of the layer of an organic light emitting medium can be made 90° C. or higher and a durability in storage of 500 hours or longer at 85° C. can be achieved.

The organic EL device of the present invention comprises the layer of an organic light emitting medium (referred to as the light emitting medium layer, hereinafter) which comprises the combination of component (A) and component (B) and is disposed between a pair of electrodes. In the organic EL device of the present invention, it is preferable that various intermediate layers are disposed between the electrodes and the light emitting medium layer. Examples of the intermediate layer include a hole injecting layer, a hole transporting layer, an electron injecting layer and an electron transporting layer. It is known that various organic and inorganic compounds can be used for these layers.

Typical examples of the construction of the organic EL device include:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

Among the above constructions, construction (8) is preferable. However, the construction of the organic EL device is not limited to the above examples.

In general, the organic EL device is prepared on a substrate which transmits light. The substrate which transmits light is the substrate which supports the organic EL device. It is preferable that the substrate which transmits light has a transmittance of light of 50% or greater in the visible region of 400 to 700 nm. It is also preferable that a flat and smooth substrate is used.

As the substrate which transmits light, for example, glass plates and synthetic resin plates are advantageously used. Specific examples of the glass plate include plates made of soda ash glass, glass containing barium and strontium, lead glass, aluminosilicate glass, borosilicate glass, barium borosilicate glass and quartz. Specific examples of the synthetic resin plates include plates made of polycarbonate resins, acrylic resins, polyethylene terephthalate resins, polyether sulfide resins and polysulfone resins.

As the anode, an electrode made of a material such as a metal, an alloy, a conductive compound and a mixture of these materials which has a great work function (4 eV or more) is preferably used. Specific examples of the material for the anode include metals such as Au and conductive materials such as CuI, ITO (indium tin oxide), $SnO_2$, ZnO and In—Zn—O. The anode can be prepared by forming a thin film of the electrode material described above in accordance with a process such as the vapor deposition process and the sputtering process. When the light emitted from the light emitting layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 μm and preferably in the range of 10 to 200 nm although the preferable range may be different depending on the used material.

As the cathode, an electrode made of a material such as a metal, an alloy, a conductive compound and a mixture of these materials which has a small work function (4 eV or smaller) is used. Specific examples of the material for the cathode include sodium, sodium-potassium alloys, magnesium, lithium, magnesium-silver alloys, aluminum/aluminum oxide, $Al/Li_2O$, $Al/LiO_2$, Al/LiF, aluminum-lithium alloys, indium and rare earth metals.

The cathode can be prepared by forming a thin film of the electrode material described above in accordance with a process such as the vapor deposition process and the sputtering process.

When the light emitted from the light emitting medium layer is obtained through the cathode, it is preferable that the cathode has a transmittance of the emitted light greater than 10%. It is also preferable that the sheet resistivity of the cathode is several hundred $\Omega/\square$ or smaller. The thickness of the cathode is, in general, selected in the range of 10 nm to 1 μm and preferably in the range of 50 to 200 nm although the preferable range may be different depending on the material used.

In the organic EL device of the present invention, it is preferable that a layer of a chalcogenide, a metal halide or a metal oxide (this layer may occasionally be referred to as a surface layer) is disposed on the surface of at least one of the pair of electrodes prepared as described above. Specifically, it is preferable that a layer of a chalcogenide (including an oxide) of a metal such as silicon and aluminum is disposed on the surface of the anode at the side of the light emitting medium layer and a layer of a metal halide or a metal oxide is disposed on the surface of the cathode at the side of the light emitting medium layer. Due to the above layers, stability in driving can be improved.

Preferable examples of the chalcogenide include $SiO_X$ ($1 \leq x \leq 2$), $AlO_X$ ($1 \leq x \leq 1.5$), SiON and SiAlON. Preferable examples of the metal halide include LiF, $MgF_2$, $CaF_2$ and fluorides of rare earth metals. Preferable examples of the metal oxide include $Cs_2O$, $Li_2O$, MgO, SrO, BaO and CaO.

In the organic EL device of the present invention, the electron transporting property and the hole transporting property of the light emitting medium layer are simultaneously improved by suitably adjusting the relative amounts of component (A) and component (B) described above and the above intermediate layers such as the hole injecting layer, the hole transporting layer and the electron injecting layer can be omitted. In this case, it is preferable that the surface layer described above is disposed.

In the organic EL device of the present invention, it is preferable that a mixed region of an electron transfer compound and a reducing dopant or a mixed region of a hole transfer compound and an oxidizing dopant is disposed on the surface of at least one of the pair of electrodes prepared as described above. Due to the mixed region disposed as described above, the electron transfer compound is reduced to form an anion and injection and transportation of electrons from the mixed region into the light emitting medium can be facilitated. The hole transfer compound is oxidized to form a cation and injection and transportation of holes from the mixed region into the light emitting medium is facilitated. Preferable examples of the oxidizing dopant include various types of Lewis acid and acceptor compounds. Preferable examples of the reducing dopant include alkali metals, compounds of alkali metals, alkaline earth metals, rare earth metals and compounds of these metals.

In the organic EL device of the present invention, the light emitting medium layer has the following functions:

(1) The injecting function: the function of injecting holes from the anode or the hole injecting layer and injecting electrons from the cathode or the electron injecting layer when an electric field is applied;

(2) The transporting function: the function of transporting injected charges (electrons and holes) by the force of the electric field; and (3) The light emitting function: the function of providing the field for recombination of electrons and holes and leading the recombination to the emission of light.

As the process for forming the light emitting medium layer, a conventional process such as the vapor deposition process, the spin coating process and the Langmuir-Blodgett process (the LB process) can be used. It is particularly preferable that the organic light emitting medium layer is a molecular deposit film. The molecular deposit film is a thin film formed by deposition of a material compound in the gas phase or a thin film formed by solidification of a material compound in a solution or in the liquid phase. In general, the molecular deposit film can be distinguished from the thin film formed in accordance with the LB process (the molecular accumulation film) based on the differences in the aggregation structure and higher order structures and functional differences caused by these structural differences.

As disclosed in Japanese Patent Application Laid-Open No. Showa 57(1982)-51781, the light emitting medium layer can also be formed by dissolving a binder such as a resin and the material compounds into a solvent to prepare a solution, followed by forming a thin film from the prepared solution in accordance with the spin coating process or the like.

In the present invention, where desired, the light emitting medium layer may comprise conventional organic light emitting media other than component (A) and component (B) described above or the light emitting medium layer comprising the compounds described in the present invention may be laminated with a light emitting medium layer comprising other conventional organic light emitting media as long as the object of the present invention is not adversely affected.

The hole injecting layer and the hole transporting layer are layers which help injection of holes into the light emitting medium layer and transport the holes to the light emitting region. The layers exhibit a great mobility of holes and, in general, have an ionization energy as small as 5.5 eV or smaller. For the hole injecting layer and the hole transporting layer, a material which transports holes to the light emitting medium layer at a small electric field strength is preferable. A material which exhibits, for example, a mobility of holes of at least $10^{-6}$ cm$^2$/V·sec under application of an electric field of $10^4$ to $10^6$ V/cm is more preferable. A material can be selected from materials which are conventionally used as the charge transporting material of holes in photoconductive materials and conventional materials which are used for the hole injecting layer in organic EL devices.

To form the hole injecting layer or the hole transporting layer, a thin film may be formed from a material for the hole injecting layer or the hole transporting layer, respectively, in accordance with a conventional process such as the vacuum vapor deposition process, the spin coating process, the casting process and the LB process. The thickness of the hole injecting layer and the hole transporting layer is not particularly limited. In general, the thickness is 5 nm to 5 nm.

The electron injection layer is a layer which helps injection of electrons into the light emitting medium layer and exhibits a great mobility of electrons. The adhesion improving layer is a layer made of a material exhibiting excellent adhesion with the cathode among the electron injecting layer. As the material for the electron injecting layer, metal complexes of 8-hydroxyquinoline and derivatives thereof are preferably used. Specific examples of the metal complex of 8-hydroxyquinoline and derivatives thereof include metal chelates of oxinoid compounds including chelates of oxine (in general, 8-quinolinol or 8-hydroxyquinoline). For example, tris(8-quinolinol)aluminum can be used as the electron injecting material.

The organic EL device of the present invention tends to form defects in pixels due to leak and short circuit since an electric field is applied to ultra-thin films. To prevent the formation of the defects, a layer of an insulating thin film may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be used.

To prepare the organic EL device of the present invention, for example, the anode, the light emitting medium layer and, where necessary, the hole injecting layer and the electron injecting layer are formed in accordance with the above process using the above materials and the cathode is formed in the last step. The organic EL device may be prepared by forming the above layers in the order reverse to that described above, i.e., the cathode being formed in the first step and the anode in the last step.

An embodiment of the process for preparing an organic EL device having a construction in which an anode, a hole injecting layer, a light emitting medium layer, an electron injecting layer and a cathode are disposed successively on a substrate which transmits light will be described in the following.

On a suitable substrate which transmits light, a thin film made of a material for the anode is formed in accordance with the vapor deposition process or the sputtering process so that the thickness of the formed thin film is 1 m or smaller and preferably in the range of 10 to 200 nm. The formed thin film is used as the anode. Then, a hole injecting layer is formed on the anode. The hole injecting layer can be formed in accordance with the vacuum vapor deposition process, the spin coating process, the casting process or the LB process, as described above. The vacuum vapor deposition process is preferable because a uniform film can be easily obtained and the possibility of formation of pin holes is small. When the hole injecting layer is formed in accordance with the vacuum vapor deposition process, in general, it is preferable that the conditions are suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C. and the thickness of the film: 5 nm to 5 μm; although the conditions of the vacuum vapor deposition are different depending on the used compound (the material for the hole injecting layer) and the crystal structure and the recombination structure of the hole injecting layer to be formed.

Then, the light emitting medium layer is formed on the hole injecting layer formed above. Using the organic light emitting medium described in the present invention, a thin film of the organic light emitting medium can be formed in accordance with the vacuum vapor deposition process, the sputtering process, the spin coating process or the casting process and the formed thin film is used as the light emitting medium layer. The vacuum vapor deposition process is preferable because a uniform film can be easily obtained and the possibility of formation of pin holes is small. When the light emitting medium layer is formed in accordance with the vacuum vapor deposition process, in general, the conditions of the vacuum vapor deposition process can be selected in the same ranges as those described for the vacuum vapor deposition of the hole injecting layer although the conditions are different depending on the used compound. It is preferable that the thickness is in the range of 10 to 40 nm.

An electron injecting layer is formed on the light emitting medium layer formed above. Similarly to the hole injecting layer and the light emitting medium layer, it is preferable that the electron injecting layer is formed in accordance with the vacuum vapor deposition process since a uniform film must be obtained. The conditions of the vacuum vapor deposition can be selected in the same ranges as those described for the vacuum vapor deposition of the hole injecting layer and the light emitting medium layer.

A cathode is formed on the electron injecting layer formed above in the last step and an organic EL device can be obtained. The cathode is made of a metal and can be formed in accordance with the vacuum vapor deposition process or the sputtering process. It is preferable that the vacuum vapor deposition process is used in order to prevent formation of damages on the lower organic layers during the formation of the film.

In the above preparation of the organic EL device, it is preferable that the above layers from the anode to the cathode are formed successively while the preparation system is kept in a vacuum after being evacuated.

The organic EL device which can be prepared as described above emits light when a direct voltage of 3 to 40 V is applied in the condition that the anode is connected to a positive electrode (+) and the cathode is connected to a negative electrode (−). When the connection is reversed, no electric current is observed and no light is emitted at all. When an alternating voltage is applied to the organic EL device, light emission is observed only in the condition that the polarity of the anode is positive and the polarity of the cathode is negative. When an alternating voltage is applied to the organic EL device, any type of wave shape can be used.

The present invention also provides the organic light emitting medium comprising component (A) and component (B) described above. The organic light emitting medium is advantageously used for the organic electroluminescence device having excellent heat resistance and a long life and efficiently emitting bluish to yellowish light.

The present invention will be described more specifically with reference to examples in the following. However, the present invention is not limited to the examples.

Example 1

On a glass plate having a size of 25×75×1.1 mm, a transparent electrode made of indium tin oxide and having a thickness of 120 nm was formed. After the glass substrate was cleaned by irradiation with ultraviolet light and exposure to ozone, the glass substrate was placed in a vacuum vapor deposition apparatus.

After N,N'-bis[4-(diphenylamino)phenyl]-N,N'-diphenyl-biphenyl-4,4'-diamine was vapor deposited so that a hole injecting layer having a thickness of 60 nm was formed, N,N,N',N'-tetrakis(4-biphenyl)-4,4'-benzidine was vapor deposited on the formed hole injecting layer so that a hole transporting layer having a thickness of 20 nm was formed. Then, compound (EM4) shown above as component (B) and compound (EM83) shown above as component (A) were simultaneously vapor deposited in amounts such that the ratio of the amount by weight of component (B) to the amount by weight of component (A) was 40:3 so that a light emitting layer having a thickness of 40 nm was formed.

On the formed light emitting layer, tris(8-hydroxyquinolinato)-aluminum (Alq) was vapor deposited so that an electron injecting layer having a thickness of 20 nm was formed. Lithium fluoride (LiF) was vapor deposited so that a layer having a thickness of 0.3 nm was formed and then aluminum (Al) was vapor deposited so that a layer having a thickness of 150 nm was formed. The formed LiF/Al film worked as the cathode. An organic EL device was prepared as described above.

The prepared organic EL device was tested by passing an electric current. Light emission of pure blue color (the half width: 42 nm) having a luminance of 205 $cd/m^2$ was obtained at a voltage of 6.5 V and a current density of 10 $mA/cm^2$. The device was tested by continuously passing a direct current at an initial luminance of 500 $cd/m^2$ and the half-life time was found to be 900 hours.

Examples 2 to 19

Organic EL devices were prepared in accordance with the same procedures as those conducted in Example 1 except that compounds shown in Table 1 were used as component (B) and component (A). The results of testing the obtained devices by passing an electric current at a current density of 10 $mA/cm^2$ are shown in Table 1. The half-life times obtained by the test of continuous passage of a direct current at initial luminances shown in Table 1 are also shown in Table 1.

Comparative Example 1

An organic EL device was prepared in accordance with the same procedures as those conducted in Example 1 except that a light emitting layer having a thickness of 40 nm was formed with compound (EM4) alone in place of the combination of compound (EM4) and compound (EM83) used in Example 1. The results of testing the obtained device by passing an electric current at a current density of 10 $mA/cm^2$ are shown in Table 1. The device was tested by continuously passing a direct current at an initial luminance of 500 $cd/m^2$ and the half-life time was found to be as short as 90 hours.

Comparative Example 2

An organic EL device was prepared in accordance with the same procedures as those conducted in Example 1 except that 4,4'-bis(diphenylamino)stilbene (H2) was used in place of compound (EM83) used in Example 1. The results of testing the obtained device by passing an electric current at a current density of 10 mA/cm² are shown in Table 1. The device was tested by continuously passing a direct current at an initial luminance of 500 cd/m² and the half-life time was found to be as short as 300 hours.

Comparative Example 3

An organic EL device was prepared in accordance with the same procedures as those conducted in Example 1 except that 2,5,8,11-tetra-t-butylperylene (H3) was used in place of compound (EM83) used in Example 1. The results of testing the obtained device by passing an electric current at a current density of 10 mA/cm² are shown in Table 1. The device was tested by continuously passing a direct current at an initial luminance of 1,000 cd/m² and the half-life time was found to be as short as 200 hours.

Comparative Example 4

An organic EL device was prepared in accordance with the same procedures as those conducted in Example 1 except that N,N'-di(naphthalen-2-yl),N,N'-diphenylbenzene (H4) was used in place of compound (EM83) used in Example 1. The results of testing the obtained device by passing an electric current at a current density of 10 mA/cm² are shown in Table 1. The device was tested by continuously passing a direct current at an initial luminance of 500 cd/m² and the half-life time was found to be as short as 200 hours.

Comparative Example 5

An organic EL device was prepared in accordance with the same procedures as those conducted in Example 11 except that 1,3-bis-[2-{4-N,N'-(diphenylamino)phenyl}vinyl]benzene (H5) was used in place of compound (EM98) used in Example 11. The results of testing the obtained device by passing an electric current at a current density of 10 mA/cm² are shown in Table 1. The device was tested by continuously passing a direct current at an initial luminance of 1,000 cd/m² and the half-life time was found to be as short as 750 hours.

Example 20

An organic EL device was prepared in accordance with the same procedures as those conducted in Example 1 except that compounds shown in Table 2 were used as component (B) and component (A) and Alq:Cs/Al was used as the cathode. Alq:Cs/Al was a mixed layer containing Alq and Cs (cesium) metal as the electron transporting compounds in relative amounts by mole of 1:1. The results of testing the obtained device by passing an electric current at a current density of 10 mA/cm² are shown in Table 2. The half-life time obtained by the test of continuous passage of a direct current at the initial luminance shown in Table 2 is also shown in Table 2.

Examples 21 and 22

An organic EL device was prepared in accordance with the same procedures as those conducted in Example 20 except that compounds shown in Table 2 were used as component (B) and component (A). The results of testing the obtained devices by passing an electric current at a current density of 10 mA/cm² are shown in Table 2. The half-life times obtained by the test of continuous passage of a direct current at initial luminances shown in Table 2 are also shown in Table 2.

TABLE 1

| | Components of light emitting layer | | Voltage (V) | Luminance of emitted light (cd/m²) | Efficiency of light emission (cd/A) |
|---|---|---|---|---|---|
| | component (B) | component (A) | | | |
| Example 1 | EM4 | EM83 | 6.5 | 205 | 2.05 |
| Example 2 | EM4 | EM110 | 6.3 | 310 | 3.10 |
| Example 3 | EM5 | EM111 | 6.0 | 325 | 3.25 |
| Example 4 | EM5 | EM77 | 6.8 | 195 | 1.95 |
| Example 5 | EM5 | EM117 | 6.0 | 295 | 2.95 |
| Example 6 | EM27 | EM110 | 6.5 | 190 | 1.90 |
| Example 7 | EM37 | EM111 | 6.0 | 180 | 1.80 |
| Example 8 | EM43 | EM110 | 6.2 | 165 | 1.65 |
| Example 9 | EM49 | EM111 | 6.3 | 170 | 1.70 |
| Example 10 | EM4 | EM60 | 6.0 | 350 | 3.50 |
| Example 11 | EM4 | EM98 | 6.0 | 730 | 7.30 |
| Example 12 | EM5 | EM60 | 6.0 | 345 | 3.45 |
| Example 13 | EM5 | EM98 | 6.0 | 815 | 8.15 |
| Example 14 | EM5 | EM97 | 6.5 | 5 | 5.50 |
| Example 15 | EM27 | EM98 | 6.0 | 355 | 3.55 |
| Example 16 | EM42 | EM97 | 6.5 | 395 | 3.95 |
| Example 17 | EM46 | EM98 | 6.0 | 500 | 5.00 |
| Example 18 | EM4 | EM89 | 7.0 | 1050 | 10.50 |
| Example 19 | EM4 | EM94 | 7.5 | 950 | 9.50 |
| Comparative Example 1 | | EM4 | 6.3 | 90 | 0.90 |
| Comparative Example 2 | EM4 | H2 | 6.8 | 105 | 1.05 |
| Comparative Example 3 | EM4 | H3 | 6.5 | 200 | 2.00 |
| Comparative Example 4 | EM4 | H4 | 7.0 | 96 | 0.96 |
| Comparative Example 5 | EM4 | H5 | 6.8 | 510 | 5.10 |

| | Color of emitted light | Half width (nm) | Half-life time (hour) | Initial luminance (cd/m²) |
|---|---|---|---|---|
| Example 1 | pure blue | 42 | 900 | 500 |
| Example 2 | pure blue | 43 | 2900 | 500 |
| Example 3 | pure blue | 45 | 3050 | 500 |
| Example 4 | pure blue | 42 | 680 | 500 |
| Example 5 | pure blue | 44 | 1000 | 500 |
| Example 6 | pure blue | 44 | 1150 | 500 |
| Example 7 | pure blue | 45 | 1200 | 500 |
| Example 8 | pure blue | 43 | 950 | 500 |
| Example 9 | pure blue | 45 | 1100 | 500 |
| Example 10 | blue | 40 | 800 | 1000 |
| Example 11 | blue | 50 | 3100 | 1000 |
| Example 12 | blue | 41 | 700 | 1000 |
| Example 13 | blue | 49 | 3200 | 1000 |
| Example 14 | blue | 48 | 2950 | 1000 |
| Example 15 | blue | 49 | 1500 | 1000 |
| Example 16 | blue | 49 | 900 | 1000 |
| Example 17 | blue | 50 | 1000 | 1000 |
| Example 18 | green | 68 | 1050 | 3000 |
| Example 19 | green | 65 | 750 | 3000 |
| Comparative Example 1 | pure blue | 45 | 90 | 500 |
| Comparative Example 2 | pure blue | 58 | 300 | 500 |
| Comparative Example 3 | green | 69 | 200 | 1000 |
| Comparative Example 4 | pure blue | 46 | 100 | 500 |
| Comparative Example 5 | blue | 62 | 500 | 1000 |

TABLE 2

| | Components of light emitting layer | | Voltage (V) | Luminance of emitted light (cd/m²) | Efficiency of light emission (cd/A) |
|---|---|---|---|---|---|
| | component (B) | component (A) | | | |
| Example 20 | EM32 | EM111 | 5.0 | 290 | 2.90 |
| Example 21 | EM4 | EM128 | 6.5 | 260 | 2.60 |
| Example 22 | EM5 | EM128 | 6.0 | 250 | 2.50 |
| Example 23 | EM42 | EM128 | 6.5 | 155 | 1.55 |
| Example 24 | EM5 | EM131 | 6.7 | 964 | 9.64 |
| Example 25 | EM5 | EM133 | 6.5 | 1015 | 10.15 |
| Example 26 | EM43 | EM139 | 7.0 | 950 | 9.50 |
| Example 27 | EM5 | EM139 | 6.5 | 2040 | 20.40 |
| Example 28 | EM42 | EM144 | 6.5 | 1050 | 10.50 |
| Example 29 | EM5 | EM144 | 6.4 | 2100 | 21.00 |
| Example 30 | EM32 | EM144 | 6.0 | 1555 | 15.60 |
| Example 31 | EM32 | EM160 | 6.5 | 1430 | 14.30 |
| Example 32 | EM32 | EM189 | 6.0 | 980 | 9.80 |
| Example 33 | Alq | EM139 | 7.0 | 1420 | 14.20 |
| Example 34 | EM4 | EM215 | 6.5 | 340 | 3.40 |
| Example 35 | EM5 | EM215 | 6.5 | 355 | 3.55 |
| Example 36 | EM42 | EM215 | 6.7 | 185 | 1.85 |
| Example 37 | EM4 | EM195 | 6.0 | 1050 | 10.50 |
| Example 38 | EM4 | EM197 | 6.4 | 1030 | 10.30 |
| Example 39 | EM5 | EM202 | 6.5 | 1870 | 18.70 |
| Example 40 | EM5 | EM204 | 6.5 | 1850 | 18.50 |
| Example 41 | EM5 | EM208 | 6.9 | 1350 | 13.50 |

| | Color of emitted light | Half width (nm) | Half-life time (hour) | Initial luminance (cd/m²) |
|---|---|---|---|---|
| Example 20 | pure blue | 44 | 1300 | 500 |
| Example 21 | pure blue | 43 | 2100 | 500 |
| Example 22 | pure blue | 43 | 2350 | 500 |
| Example 23 | pure blue | 44 | 1000 | 500 |
| Example 24 | blue | 49 | 4000 | 1000 |
| Example 25 | blue | 50 | 4100 | 1000 |
| Example 26 | green | 68 | 900 | 3000 |
| Example 27 | green | 67 | 4500 | 3000 |
| Example 28 | green | 67 | 1100 | 3000 |
| Example 29 | green | 68 | 4750 | 3000 |
| Example 30 | green | 68 | 1050 | 3000 |
| Example 31 | green | 64 | 1800 | 3000 |
| Example 32 | green | 65 | 950 | 3000 |
| Example 33 | green | 69 | 1500 | 3000 |
| Example 34 | pure blue | 44 | 3500 | 500 |
| Example 35 | pure blue | 44 | 3950 | 500 |
| Example 36 | pure blue | 43 | 970 | 500 |
| Example 37 | blue | 50 | 4050 | 1000 |
| Example 38 | blue | 49 | 3950 | 1000 |
| Example 39 | green | 68 | 2100 | 3000 |
| Example 40 | green | 68 | 1950 | 3000 |
| Example 41 | green | 65 | 1500 | 3000 |

As shown in Table 1 and Table 2, the excellent efficiencies and the excellent lives could be achieved in the devices emitting green light, blue light and pure blue light, which was hard to obtain, as shown in Examples 1 to 41. The above results were achieved since the light having more excellent purity of color could be emitted due to the decrease in the half width in comparison to those of the devices of Comparative Examples.

In particular, the devices comprising the diaminoanthracene derivatives emitting green light, the diaminopyrene derivatives emitting blue light and the diaminochrysene derivatives emitting pure blue light as component (A) exhibited more excellent efficiencies of light emission and lives in comparison to those of any of the devices of Comparative Examples.

Since the anthracene derivative was used as component (B) and the diaminoanthracene derivative, the diaminopyrene derivative or the diaminochrysene derivative was used as component (A), the most excellent efficiency of light emission and life could be achieved by the devices emitting green light, blue light and pure blue light.

INDUSTRIAL APPLICABILITY

In accordance with the present invention, the organic EL device which exhibits excellent purity of color, has excellent heat resistance and a long life and efficiently emits bluish to yellowish light and an organic light emitting medium which can be advantageously used for the organic electroluminescence device, can be provided.

The organic EL device can be advantageously used as the light emitting device in various types of display apparatuses and is particularly suitable for full color display apparatuses.

The invention claimed is:
1. An electroluminescence device comprising a pair of electrodes and a layer of an organic light emitting medium disposed between the pair of electrodes, wherein the layer of an organic light emitting medium comprises:
(A) an arylamine compound according to formula (V):

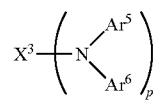

(V)

wherein:
X$^3$ is a substituted or unsubstituted residue of naphthalene, phenanthrene, fluoranthene, anthracene, pyrene, perylene, coronene, chrysene, picene, diphenylanthracene, fluorene, triphenylene, rubicene, benzoanthracene, phenylanthracene, bisanthracene, dianthracenylbenzene, or dibenzoanthracene;
each Ar$^5$ and Ar$^6$ is independently a substituted or unsubstituted monovalent aromatic group having 6 to 40 carbon atoms; and
p is an integer of 1 to 4; and
(B) a compound having a condensed ring according to formula (IV):

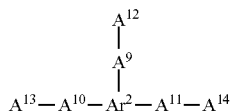

(IV)

wherein:
Ar$^2$ is a substituted or unsubstituted anthracene residue;
each of A$^9$ to A$^{11}$ is independently a substituted or unsubstituted arylene group having 6 to 40 carbon atoms;
each of A$^{12}$ to A$^{14}$ is independently a hydrogen atom, an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, a nitro group, a cyano group, an ester group having 1 to 6 carbon atoms or a halogen atom;
at least one of A$^9$ to A$^{14}$ is a group having condensed aromatic rings; and each substituent of each substituted group in formula (IV) is independently selected from the group consisting of an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, a nitro group, a cyano group, an ester group having 1 to 6 carbon atoms, and a halogen atom; and wherein the organic light emitting medium is free of styrylaryl compounds.

2. The electroluminescence device according to claim 1, wherein each of $Ar^5$ and $Ar^6$ is selected from the group consisting of a phenyl group, a naphthyl group, an anthranyl group, a phenanthryl group, a pyrenyl group, a coronyl group, a biphenyl group, a terphenyl group, a fluorenyl group, a furanyl group, a thienyl group, a benzothienyl group, an indolyl group, and a carbazolyl group.

3. The electroluminescence device according to claim 1, wherein each substituent of each substituted group in formula (V) is independently selected from the group consisting of an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, an acylamino group having 5 to 16 carbon atoms, a nitro group, a cyano group, an ester group having 1 to 6 carbon atoms, and a halogen atom.

4. The electroluminescence device according to claim 1, wherein p is 2.

5. The electroluminescence device according to claim 1, wherein $A^9$ to $A^{11}$ are each independently a substituted or unsubstituted divalent residue of benzene, biphenyl, terphenyl, phenanthrene, fluoranthene, anthracene, pyrene, perylene, coronene, chrysene, picene, fluorene, carbazole, rubicene, benzoanthracene, or dibenzoanthracene.

6. The electroluminescence device according to claim 1, wherein:
when any of $A^{12}$ to $A^{14}$ is an alkyl group having 1 to 6 carbon atoms, the alkyl group is selected from the group consisting of a methyl group, an ethyl group, a propyl group, an isopropyl group, a butyl group, an isobutyl group, a sec-butyl group, a tert-butyl group, various types of pentyl group, and various types of hexyl group;
when any of $A^{12}$ to $A^{14}$ is a cycloalkyl group having 3 to 6 carbon atoms, the cycloalkyl group is selected from the group consisting of a cyclopropyl group, a cyclobutyl group, a cyclopentyl group, and a cyclohexyl group;
when any of $A^{12}$ to $A^{14}$ is an alkoxyl group having 1 to 6 carbon atoms, the alkoxyl group is selected from the group consisting of a methoxyl group, an ethoxyl group, a propoxyl group, an isopropoxyl group, a butoxyl group, an isobutoxyl group, a sec-butoxyl group, a tert-butoxyl group, various types of pentyloxyl groups, and various types of hexyloxyl groups;
when any of $A^{12}$ to $A^{14}$ is an aryloxyl group having 5 to 18 carbon atoms, the aryloxyl group is selected from the group consisting of a phenoxyl group, a tolyloxyl group, and a naphthyloxyl group;
when any of $A^{12}$ to $A^{14}$ is an aralkyloxyl group having 7 to 18 carbon atoms, the aralkyloxyl group is selected from the group consisting of a benzyloxyl group, a phenetyloxyl group, and a naphthylmethoxyl group;
when any of $A^{12}$ to $A^{14}$ is an ester group having 1 to 6 carbon atoms, the ester group is selected from the group consisting of a methoxycarbonyl group, an ethoxycarbonyl group, a propoxycarbonyl group, and an isopropoxycarbonyl group; and
when any of $A^{12}$ to $A^{14}$ is a halogen atom, the halogen atom is selected from the group consisting of a fluorine atom, a chlorine atom, and a bromine atom.

7. The electroluminescence device according to claim 1, wherein a weight ratio of component (A) to component (B) in the organic light emitting medium is 1:99 to 20:80.

8. The electroluminescence device according to claim 1, wherein a layer of a chalcogenide, a layer of a metal halide, or a layer of a metal oxide is disposed on at least one surface of the pair of electrodes.

9. The electroluminescence device according to claim 1, wherein a mixed region comprising a reducing dopant and organic substances or a mixed region comprising an oxidizing dopant and organic substances is disposed on at least one surface of the pair of electrodes.

10. The electroluminescence device according to claim 1, wherein a thickness of the layer of an organic light emitting medium is from 10 to 40 nm.

11. An electroluminescence device comprising a pair of electrodes and a layer of an organic light emitting medium disposed between the pair of electrodes, wherein the layer of an organic light emitting medium comprises:

(A) an arylamine compound according to formula (V-a):

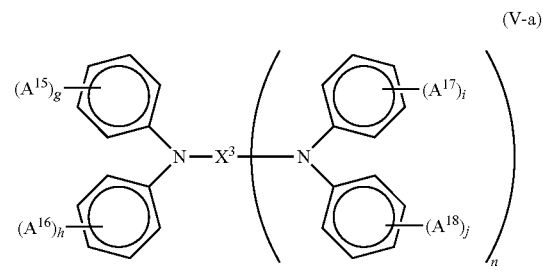

(V-a)

wherein:
$X^3$ is a substituted or unsubstituted residue of naphthalene, phenanthrene, fluoranthene, anthracene, pyrene, perylene, coronene, chrysene, picene, diphenylanthracene, fluorene, triphenylene, rubicene, benzoanthracene, phenylanthracene, bisanthracene, dianthracenylbenzene, or dibenzoanthracene;

each of $A^{15}$ to $A^{18}$ is independently a hydrogen atom, a substituted or unsubstituted alkyl group having 1 to 50 carbon atoms, a substituted or unsubstituted aryl group having 5 to 50 carbon atoms, a substituted or unsubstituted aralkyl group having 7 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxyl group having 5 to 50 carbon atoms, a substituted or unsubstituted arylamino group having 5 to 50 carbon atoms, or a substituted or unsubstituted alkylamino group having 1 to 20 carbon atoms;

each of g, h, i, and j is an integer of 0 to 5, provided that at least one of g, h, i and j is 1 or greater and at least one of $A^{15}$ to $A^{18}$ is a substituted or unsubstituted secondary or tertiary alkyl group having 3 to 10 carbon atoms;

when any of g, h, i, and j is an integer of 2 or greater, two or more of $A^{15}$ to $A^{18}$ may be the same or different and may be bonded to each other to form a saturated or unsaturated ring; and n is an integer of 0 to 3;

or an arylamine compound according to formula (V-b):

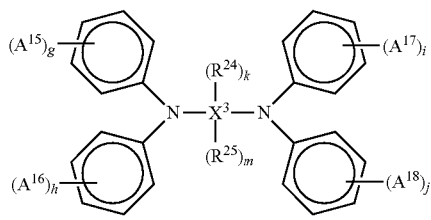

(V-b)

wherein:

$X^3$, $A^{15}$ to $A^{18}$, g, h, i, and j are as defined in formula (V-a);

each of $R^{24}$ and $R^{25}$ is independently a hydrogen atom, a substituted or unsubstituted alkyl group having 1 to 10 carbon atoms, a substituted or unsubstituted aryl group having 6 to 20 carbon atoms, a substituted or unsubstituted aralkyl group having 7 to 50 carbon atoms, a substituted or unsubstituted alkoxyl group having 1 to 50 carbon atoms, or a substituted or unsubstituted aryloxyl group having 5 to 50 carbon atoms; and each of k and m is an integer of 0 to 2, provided that at least one of k and m is 1 or greater and at least one of $R^{24}$ and $R^{25}$ is a substituted or unsubstituted secondary or tertiary alkyl group having 3 to 10 carbon atoms; and (B) a compound having a condensed ring according to formula (IV):

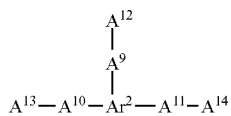

(IV)

wherein:

$Ar^2$ is a substituted or unsubstituted anthracene residue;

$A^9$ to $A^{11}$ are each independently a substituted or unsubstituted arylene group having 6 to 40 carbon atoms;

$A^{12}$ to $A^{14}$ are each independently a hydrogen atom, an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, a nitro group, a cyano group, an ester group having 1 to 6 carbon atoms, or a halogen atom;

at least one of $A^9$ to $A^{14}$ is a group having condensed aromatic rings;

each substituent of each substituted group in formula (IV) is independently selected from the group consisting of an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, a nitro group, a cyano group, an ester group having 1 to 6 carbon atoms, and a halogen atom; and the organic light emitting medium does not include a styrylaryl compound.

* * * * *